(12) United States Patent
Chappa et al.

(10) Patent No.: US 6,465,178 B2
(45) Date of Patent: *Oct. 15, 2002

(54) TARGET MOLECULE ATTACHMENT TO SURFACES

(75) Inventors: Ralph A. Chappa, Prior Lake; Sheau-Ping Hu, Falcon Heights; Dale G. Swan, St. Louis Park; Melvin J. Swanson, Carver; Patrick E. Guire, Eden Prairie, all of MN (US)

(73) Assignee: Surmodics, Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 72 days.

This patent is subject to a terminal disclaimer.

(21) Appl. No.: 09/227,913

(22) Filed: Jan. 8, 1999

(65) Prior Publication Data

US 2001/0014448 A1 Aug. 16, 2001

Related U.S. Application Data

(63) Continuation-in-part of application No. 08/940,213, filed on Sep. 30, 1997, now Pat. No. 5,858,653.

(51) Int. Cl.[7] .............................. C12Q 1/68; C12M 1/36; G01N 15/06; C07H 21/04
(52) U.S. Cl. ..................... 435/6; 435/174; 435/287.2; 435/287.9; 422/68.1; 536/23.1; 536/24.3
(58) Field of Search ....................... 435/6, 174, 287.2, 435/287.9; 422/68.1; 536/23.1, 24.3

(56) References Cited

U.S. PATENT DOCUMENTS

| | | | |
|---|---|---|---|
| 4,722,906 A | 2/1988 | Guire | 436/501 |
| 4,973,493 A | 11/1990 | Guire | 427/2 |
| 4,979,959 A | 12/1990 | Guire | 623/66 |
| 5,002,582 A | 3/1991 | Guire et al. | 623/66 |
| 5,217,492 A | 6/1993 | Guire et al. | 623/11 |
| 5,414,075 A | 5/1995 | Swan et al. | 568/333 |
| 5,510,084 A | 4/1996 | Cros et al. | 422/104 |
| 5,512,329 A | 4/1996 | Guire et al. | 623/66 |
| 5,563,056 A | 10/1996 | Swan et al. | 435/180 |
| 5,580,697 A | 12/1996 | Keana et al. | 430/296 |
| 5,610,287 A | 3/1997 | Nikiforov et al. | 536/24.3 |
| 5,637,460 A | 6/1997 | Swan et al. | 435/6 |
| 5,643,580 A | 7/1997 | Subramaniam | 422/400 |
| 5,654,162 A | 8/1997 | Guire et al. | 435/7.92 |
| 5,663,318 A * | 9/1997 | Pegg et al. | 536/24.3 |
| 5,707,818 A | 1/1998 | Chudzik et al. | 435/7.93 |
| 5,718,726 A | 2/1998 | Amon et al. | 623/2 |
| 5,744,515 A | 4/1998 | Clapper | 523/113 |
| 5,807,522 A | 9/1998 | Brown et al. | 422/50 |
| 5,858,653 A | 1/1999 | Duran et al. | 435/6 |
| 6,057,100 A | 5/2000 | Heyneker | 435/6 |

FOREIGN PATENT DOCUMENTS

| | | |
|---|---|---|
| WO | WO 91/16425 | 10/1991 |
| WO | WO 97/16544 | 5/1997 |
| WO | WO 97/34935 | 9/1997 |
| WO | WO 99/08717 | 2/1999 |
| WO | PCT/US98/20140 | 4/1999 |

OTHER PUBLICATIONS

"Microchip Arrays Put DNA on the Spot", R. Service, Science 282(5388):396–399, Oct. 16, 1998.
"Fomenting a Revolution, in Miniature", I. Amato, Science 282(5388): 402–405, Oct. 16, 1998.
"The Development of Microfabricated Arrays of DNA Sequencing and Analysis", O'Donnell–Maloney et al., TIBTECH 14:401–407 (1996).
Nunc Tech Note vol. 3, No. 17 date unavailable.
"Instructions—Reacti–Bind™ DNA Coating Solution" Jan. 1997.
DNA–Bind™ "Application Guide" date unavailable.
"Polymeric Phosphonium Salts as a Novel Class of Cationic Biocides. VII. Synthesis and Antibacterial Activity of Polymeric Phosphonium Salts and Their Model Compounds Containing Long Alkyl Chains", J. Appl. Polymer Sci. 53:1237–1244 (1994).
"Rapid detection of Salmonella subspecies I by PCT combined with non–radioactive hybridisation using covalently immobilised ligonucleotide on a microplate", Chevier et al. FEMS 10:245, 1995.

* cited by examiner

Primary Examiner—W. Gary Jones
Assistant Examiner—B J Forman
(74) Attorney, Agent, or Firm—Merchant & Gould P.C.

(57) ABSTRACT

Method and reagent composition for covalent attachment of target molecules, such as nucleic acids, onto the surface of a substrate. The reagent composition includes groups capable of covalently binding to the target molecule. Optionally, the composition can contain photoreactive groups for use in attaching the reagent composition to the surface. The reagent composition can be used to provide activated slides for use in preparing microarrays of nucleic acids.

16 Claims, No Drawings

SEQUENCE LISTING

<160> NUMBER OF SEQ ID NOS: 9

<210> SEQ ID NO 1
<211> LENGTH: 50
<212> TYPE: DNA
<213> ORGANISM: Homo sapiens

<400> SEQUENCE: 1
gtctgagtcg gagccagggc ggccgccaac agcaggagca gcgtgcacgg         50

<210> SEQ ID NO 2
<211> LENGTH: 30
<212> TYPE: DNA
<213> ORGANISM: Homo sapiens

<400> SEQUENCE: 2
gtctgagtcg gagccagggc ggccgccaac                               30

<210> SEQ ID NO 3
<211> LENGTH: 50
<212> TYPE: DNA
<213> ORGANISM: Homo sapiens

<400> SEQUENCE: 3
ccgtgcacgc tgctcctgct gttggcggcc gccctggctc cgactcagac         50

<210> SEQ ID NO 4
<211> LENGTH: 50
<212> TYPE: DNA
<213> ORGANISM: Homo sapiens

<400> SEQUENCE: 4
cggtggatgg agcaggaggg gcccgagtat tgggagcggg agacacagaa         50

<210> SEQ ID NO 5
<211> LENGTH: 30
<212> TYPE: DNA
<213> ORGANISM: Homo sapiens

<400> SEQUENCE: 5
ttctgtgtct cccgctccca atactcgggc                               30

<210> SEQ ID NO 6
<211> LENGTH: 30
<212> TYPE: DNA
<213> ORGANISM: Homo sapiens

<400> SEQUENCE: 6
ttctgtgtct cccgctccca atactcgggc                               30

<210> SEQ ID NO 7
<211> LENGTH: 30
<212> TYPE: DNA
<213> ORGANISM: Homo sapiens

<400> SEQUENCE: 7
gtctgagtcg gagccagggc ggccgccaac                               30

<210> SEQ ID NO 8
<211> LENGTH: 50
<212> TYPE: DNA
<213> ORGANISM: Homo sapiens

-continued

```
<400> SEQUENCE: 8
cggtggatgg agcaggaggg gcccgagtat tgggagcggg agacacagaa          50

<210> SEQ ID NO 9
<211> LENGTH: 20
<212> TYPE: DNA
<213> ORGANISM: Homo sapiens

<400> SEQUENCE: 9
acgccgagtt aacgccatca                                           20
```

TARGET MOLECULE ATTACHMENT TO SURFACES

CROSS REFERENCE TO RELATED APPLICATIONS

The present application is a continuation-in-part of U.S. patent application Ser. No. 08/940,213, for "Reagent and Method for Attaching Target Molecules to a Surface", filed Sep. 30, 1997, now U.S. Pat. No. 5,858,653, the entire disclosure of which is incorporated herein by reference.

TECHNICAL FIELD

The present invention relates to methods for attaching target molecules such as oligonucleotides (oligos) to a surface, and to compositions for use in such methods. In another aspect, the invention relates to the resultant coated surfaces themselves. In yet another aspect, the invention relates to the use of photochemical and thermochemical means to attach molecules to a surface.

BACKGROUND OF THE INVENTION

The immobilization of deoxyribonucleic acid (DNA) onto support surfaces has become an important aspect in the development of DNA-based assay systems as well as for other purposes, including the development of microfabricated arrays for DNA analysis. See, for instance, "Microchip Arrays Put DNA on the Spot", R. Service, Science 282 (5388):396–399, 16 October 1998; and "Fomenting a Revolution, in Miniature", I. Amato, Science 282(5388): 402–405, Oct. 16, 1998.

See also, "The Development of Microfabricated Arrays of DNA Sequencing and Analysis", O'Donnell-Maloney et al., TIBTECH 14:401–407 (1996). Generally, such procedures are carried out on the surface of microwell plates, tubes, beads, microscope slides, silicon wafers or membranes. Certain approaches, in particular, have been developed to enable or improve the likelihood of end-point attachment of a synthetic oligonucleotide to a surface. End-point attachment (i.e., with the nucleic acid sequence attached through one or the other terminal nucleotide) is desirable because the entire length of the sequence will be available for hybridization to another nucleic acid sequence. This is particularly advantageous for the detection of single base pair changes under stringent hybridization conditions.

Hybridization is the method used most routinely to measure nucleic acids by base pairing to probes immobilized on a solid support. When combined with amplification techniques such as the polymerase chain reaction (PCR) or ligase chain reaction (LCR), hybridization assays are a powerful tool for diagnosis and research. Microwell plates, in particular, are convenient and useful for assaying relatively large numbers of samples. Several methods have been used for immobilization of nucleic acid probes onto microwell plates. Some of these involve adsorption of unmodified or modified oligonucleotides onto polystyrene plates. Others involve covalent immobilization. Various methods have also been used to increase the sensitivity of hybridization assays. Polymeric capture probes (also known as target molecules) and detection probes have been synthesized and used to obtain sensitivities down to $10^7$ DNA molecules/ml. Another method used branched oligonucleotides to increase the sensitivity of hybridization assays. Yet another method used a multi-step antibody-enhanced method. Other types of nucleic acid probes such as ribonucleic acid (RNA), complementary DNA (cDNA) and peptide nucleic acids (PNA's) have also been immobilized onto microwell plates for hybridization of PCR products in diagnostic applications. Furthermore, PCR primers have been immobilized onto microwell plates for solid phase PCR.

Only a relative few approaches to immobilizing DNA, to date, have found their way into commercial products. One such product is known as "NucleoLink™", and is available from Nalge Nunc International (see, e.g., Nunc Tech Note Vol. 3, No. 17). In this product, the DNA is reacted with a carbodiimide to activate 5'-phosphate groups which then react with functional groups on the surface. Disadvantages of this approach are that it requires the extra step of adding the carbodiimide reagent as well as a five hour reaction time for immobilization of DNA, and it is limited to a single type of substrate material.

As another example, Pierce has recently introduced a proprietary DNA immobilization product known as "Reacti-Bind™ DNA Coating Solutions" (see "Instructions—Reacti-Bind™ DNA Coating Solution" 1/1997). This product is a solution that is mixed with DNA and applied to surfaces such as polystyrene or polypropylene. After overnight incubation, the solution is removed, the surface washed with buffer and dried, after which it is ready for hybridization. Although the product literature describes it as being useful for all common plastic surfaces used in the laboratory, it does have some limitations. For example, Applicants were not able to demonstrate useful immobilization of DNA onto polypropylene using the manufacturer's instructions. Furthermore, this product requires large amounts of DNA. The instructions indicate that the DNA should be used at a concentration between 0.5 and 5 $\mu$g/ml.

Similarly, Costar sells a product called "DNA-BINDTM" for use in attaching DNA to the surface of a well in a microwell plate (see, e.g., the DNA-BINDTM "Application Guide"). The surface of the DNA-BIND™ plate is coated with an uncharged, nonpolymeric heterobifunctional reagent containing an N-oxysuccinimide (NOS) reactive group. This group reacts with nucleophiles such as primary amines. The heterobifunctional coating reagent also contains a photochemical group and spacer arm which covalently links the reactive group to the surface of the polystyrene plate. Thereafter, amine-modified DNA can be covalently coupled to the NOS surface. The DNA is modified by adding a primary amine either during the synthesis process to the nascent oligomer or enzymatically to the preformed sequence. Since the DNA-BIND™ product is polystyrene based, it is of limited use for those applications that require elevated temperatures such as thermal cycling.

These various products may be useful for some purposes, or under certain circumstances, but all tend to suffer from one or more drawbacks and constraints. In particular, they either tend to require large amounts of oligonucleotide, render background noise levels that are unsuitably high and/or lack versatility.

International Patent Application No. PCT/US98/20140, assigned to the assignee of the present application, describes and claims, inter alia, a reagent composition for attaching a target molecule to the surface of a substrate, the reagent composition comprising one or more groups for attracting the target molecule to the reagent, and one or more thermochemically reactive groups for forming covalent bonds with corresponding functional groups on the attracted target molecule. Optionally, the composition further provides photogroups for use in attaching the composition to a surface. In one embodiment, for instance, a plurality of photogroups and a plurality of cationic groups (in the form of quaternary ammonium groups) are attached to a hydrophilic polymer backbone. This polymer can then be coimmobilized with a second polymer backbone that provides the above-described thermochemically reactive groups (e.g., N-oxysuccinimide ("NOS") groups) for immobilization of target molecules.

While reagent compositions having both attracting groups and thermochemically reactive groups, as described in the above-captioned PCT application, remain useful and preferred for many applications, Applicants also find that the attracting groups may not be required under all circumstances. For instance, one suitable process for preparing activated slides for microarrays includes the steps of coating the slides with a reagent composition of a type described in the PCT application (and particularly, one having both attracting groups as well as photoreactive and thermochemically reactive groups). The polymers are attached to the slide by activation of the photoreactive groups, following by the application of small volumes (e.g., several nanoliters or less) of target molecules (e.g., oligonucleotides) using precision printing techniques.

Once applied, the solvent used to deliver the oligonucleotide is dried (as the oligonucleotides are attracted to the bound polymer), and the slide incubated under conditions suitable to permit the thermochemical coupling of the oligonucleotide to the bound polymer. Thereafter, however, any unbound oligonucleotide is typically washed off of the slide. Applicants have found, however, that there occasionally remains a detectable trail of unbound oligonucleotide, referred to as a "comet effect", leading away from the spot. This trail is presumably due to the attractive forces within the bound polymer present on the slide surface that surrounds the spot, serving to tie up the generally negatively charged oligonucleotide as it is washed from the spot. This trail, in turn, can provide undesirable and unduly high levels of background noise.

Applicants have found that under such circumstances (e.g., the application of small volumes directly to a generally flat surface) polymeric reagents are preferably provided without the presence of such attracting groups (though with the thermochemically reactive groups and optional photogroups). Suitable reagents of this type are disclosed in the above-captioned co-pending PCT application. Such reagents, in turn, can be used to coat oligonucleotides in a manner that provides an improved combination of such properties as reduced background, small spot size (e.g., increased contact angle), as compared to polymeric reagents having charged attracting groups.

SUMMARY OF THE INVENTION

The present invention provides a method and reagent composition for covalent attachment of target molecules onto the surface of a substrate, such as microwell plates, tubes, beads, microscope slides, silicon wafers or membranes. In one embodiment, the method and composition are used to immobilize nucleic acid probes onto plastic materials such as microwell plates, e.g., for use in hybridization assays. In a preferred embodiment the method and composition are adapted for use with substantially flat surfaces, such as those provided by microscope slides and other plastic, silicon hydride, or organosilane-pretreated glass or silicone slide support surfaces. The reagent composition can then be used to covalently attach a target molecule such as a biomolecule (e.g., a nucleic acid) which in turn can be used for specific binding reactions (e.g., to hybridize a nucleic acid to its complementary strand).

Support surfaces can be prepared from a variety of materials, including but not limited to plastic materials selected from the group consisting of crystalline thermoplastics (e.g., high and low density polyethylenes, polypropylenes, acetal resins, nylons and thermoplastic polyesters) and amorphous thermoplastics (e.g., polycarbonates and poly(methyl methacrylates). Suitable plastic or glass materials provide a desired combination of such properties as rigidity, toughness, resistance to long term deformation, recovery from deformation on release of stress, and resistance to thermal degradation.

A reagent composition of the invention contains one or more thermochemically reactive groups (i.e., groups having a reaction rate dependent on temperature). Suitable groups are selected from the group consisting of activated esters (e.g., NOS), epoxide, azlactone, activated hydroxyl and maleimide groups. Optionally, and preferably, the composition can also contain one or more photoreactive groups. Additionally, the reagent may comprise one or more hydrophilic polymers, to which the thermochemically reactive and/or photoreactive groups can be pendent. The photoreactive groups (alternatively referred to herein as "photogroups") can be used, for instance, to attach reagent molecules to the surface of the support upon the application of a suitable energy source such as light. The thermochemically reactive groups, in turn, can be used to form covalent bonds with appropriate and complementary functional groups on the target molecule.

Generally, the reagent molecules will first be attached to the surface by activation of the photogroups, thereafter the target molecule, (e.g., an oligonucleotide) is contacted with the bound reagent under conditions suitable to permit it to come into binding proximity with the bound polymer. The target molecule is thermochemically coupled to the bound reagent by reaction between the reactive groups of the bound reagent and appropriate functional groups on the target molecule. The thermochemically reactive groups and the ionic groups can either be on the same polymer or, for instance, on different polymers that are coimmobilized onto the surface. Optionally, and preferably, the target molecule can be prepared or provided with functional groups tailored to groups of the reagent molecule. During their synthesis, for instance, the oligonucleotides can be prepared with functional groups such as amines or sulfhydryl groups.

The invention further provides a method of attaching a target molecule, such as an oligo, to a surface, by employing a reagent as described herein. In turn, the invention provides a surface having nucleic acids attached thereto by means of such a reagent, as well as a material (e.g., microwell plate) that provides such a surface. In yet another aspect, the invention provides a composition comprising a reagent(s) of this invention in combination with a target molecule that contains one or more functional groups reactive with the thermochemically reactive group(s) of the reagent.

Using such reagents, applicants have found that capture probes can be covalently immobilized to a variety of surfaces, including surfaces that would not otherwise adsorb the probes (such as polypropylene and polyvinylchloride). The resulting surfaces provide signals comparable to or better than those obtained with modified oligonucleotides adsorbed onto polystyrene or polycarbonate.

The present immobilization reagent and method can be used in amplification methods in a manner that is simpler than those previously reported, and can also provide improved surfaces for the covalent immobilization of nucleophile-derivatized nucleic acids. In addition to immobilized probes for amplification methods and hybridization assays, the reagents of this invention may provide improved nucleic acid immobilization for solid phase sequencing and for immobilizing primers for PCR and other amplification techniques.

DETAILED DESCRIPTION

A preferred reagent molecule of the present invention comprises a hydrophilic backbone bearing one or more thermochemically reactive groups useful for forming a covalent bond with the corresponding functional group of the target molecule, together with one or more photoreactive groups useful for attaching the reagent to a surface.

In another embodiment of the invention, it is possible to immobilize nucleic acid sequences without the use of the photoreactive group. For instance, the surface of the material to be coated can be provided with thermochemically reactive groups, which can be used to immobilize hydrophilic polymers having thermochemically reactive groups as described above. For example, a surface may be treated with an ammonia plasma to introduce a limited number of reactive amines on the surface of the material. If this surface is then treated with a hydrophilic polymer having thermochemically reactive groups (e.g., NOS groups), then the polymer can be immobilized through reaction of the NOS groups with corresponding amine groups on the surface. Preferably, the reactive groups on the polymer are in excess relative to the corresponding reactive groups on the surface to insure that a sufficient number of these thermochemically reactive groups remain following the immobilization to allow coupling with the nucleic acid sequence.

While not intending to be bound by theory, it appears that by virtue of the small spot size, as well as the kinetics and fluid dynamics encountered in the use of reduced spot sizes, the oligonucleotide is able to come into binding proximity with the bound reagent without the need for the attracting groups described above. When used for preparing microarrays, e.g., to attach capture molecules (e.g., oligonucleotides or cDNA) to the microarray surface, such capture molecules are generally delivered to the surface in a volume of less than about 1 nanoliter per spot, using printing pins adapted to form the spots into arrays having center to center spacing of about 200 $\mu$m to about 500 $\mu$m.

Given their small volumes, the printed target arrays tend to dry quickly, thus further affecting the coupling kinetics and efficiency. Unlike the coupling of DNA from solution and onto the surface of coated microplate wells, oligonucleotides printed in arrays of extremely small spot sizes tend to dry quickly, thereby altering the parameters affecting the manner in which the oligonucleotides contact and couple with the support. In addition to the design and handling of the printing pins, other factors can also affect the spot size, and in turn, the ultimate hybridization signals, including: salt concentrations, type of salts and wetting agents in the printing buffer; hydrophobic/hydrophilic properties of the surfaces; the size and/or concentration of the oligonucleotide; and the drying environments.

As described herein (e.g., in Examples 25, 26 and 28), coatings of reagents having both photogroups and thermochemically reactive groups ("Photo-PA-PolyNOS"), as well as reagents having those groups together with attracting groups (a mixture of "Photo-PA-PolyNOS/Photo-PA-PolyQuat") both provided useful and specific immobilization of amine-modified DNA, with the choice between the two approaches being largely dependent on the choice of substrate (e.g., flat slide as opposed to microwell).

In a preferred embodiment, the reagent composition can be used to prepare activated slides having the reagent composition photochemically immobilized thereon. The slides can be stably stored and used at a later date to prepare microarrays by immobilizing amine-modified DNA. The coupling of the capture DNA to the surface takes place at pH 8–9 in a humid environment following printing the DNA solution in the form of small spots.

Activated slides of the present invention are particularly well suited to replace conventional (e.g., silylated) glass slides in the preparation of microarrays using manufacturing and processing protocols, reagents and equipment such as micro-spotting robots (e.g., as available from Cartesian), and a chipmaker micro-spotting device (e.g., as available from TeleChem International). Suitable spotting equipment and protocols are commercially available, such as the "ArrayIt"™ ChipMaker 3 spotting device. This product is said to represent an advanced version of earlier micro-spotting technology, employing 48 printing pins to deliver as many as 62,000 samples per solid substrate.

The use of such an instrument, in combination with conventional (e.g., poly-1-lysine coated) slides, is well known in the art. See, for instance, U.S. Pat. No. 5,087,522 (Brown et al.) "Methods for Fabricating Microarrays of Biological Samples", and the references cited therein, the disclosures of each of which are incorporated herein by reference.

For instance, the method and system of the present invention can be used to provide a substrate, such as a glass slide, with a surface having one or more microarrays. Each microarray preferably provides at least about 100/cm$^2$ (and preferably at least about 1 000/cm$^2$) distinct target molecules (e.g., polynucleotide or polypeptide biopolymers) in a surface area of less than about 1 cm$^2$. Each distinct target molecule (1) is disposed at a separate, defined position in the array, (2) has a length of at least 10 subunits, (3) is present in a defined amount between about 0.1 femtomoles and about 10 nanomoles, and (4) is deposited in selected volume in the volume range of about 0.01 nanoliters to about 100 nanoliters. These regions (e.g., discrete spots) within the array can be generally circular in shape, with a typical diameter of between about 10 microns and about 500 microns (and preferably between about 20 and about 200 microns). The regions are also preferably separated from other regions in the array by about the same distance (e.g., center to center spacing of about 20 microns to about 1000 microns) . A plurality of analyte-specific regions can be provided, such that each region includes a single, and preferably different, analyte specific reagent ("target molecule").

Those skilled in the art, given the present description, will be able to identify and select suitable reagents depending on the type of target molecule of interest. Target molecules include, but are not limited to, plasmid DNA, cosmid DNA, bacteriophage DNA, genomic DNA (includes, but not limited to yeast, viral, bacterial, mammalian, insect), RNA, cDNA, PNA, and oligonucleotides.

A polymeric backbone can be either synthetic or naturally occurring, and is preferably a synthetic polymer selected from the group consisting of oligomers, homopolymers, and copolymers resulting from addition or condensation polymerization. Naturally occurring polymers, such as polysaccharides, polypeptides can be used as well. Preferred backbones are biologically inert, in that they do not provide a biological function that is inconsistent with, or detrimental to, their use in the manner described.

Such polymer backbones can include acrylics such as those polymerized from hydroxyethyl acrylate, hydroxyethyl methacrylate, glyceryl acrylate, glyceryl methacrylate, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide, polyurethanes and polyethers (e.g., polyethylene oxides).

The polymeric backbones of the invention are chosen to provide hydrophilic backbones capable of bearing the desired number and type of thermochemically reactive groups, and optionally photogroups, the combination dependent upon the reagent selected. The polymeric backbone is also selected to provide a spacer between the surface and the thermochemically reactive groups. In this manner, the reagent can be bonded to a surface or to an adjacent reagent molecule, to provide the other groups with sufficient freedom of movement to demonstrate optimal activity. The polymer backbones are preferably hydrophilic (e.g., water soluble), with polyacrylamide and polyvinylpyrrolidone being particularly preferred polymers.

Reagents of the invention carry one or more pendent latent reactive (preferably photoreactive) groups covalently bound (directly or indirectly) to the polymer backbone.

Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene. Photoactivatible aryl ketones such as benzophenone and acetophenone are of particular importance inasmuch as these groups are subject to multiple reactivation in water and hence provide increased coating efficiency.

Upon activation of the photoreactive groups, the reagent molecules are covalently bound to each other and/or to the material surface by covalent bonds through residues of the photoreactive groups. Exemplary photoreactive groups, and their residues upon activation, are shown as follows.

| Photoreactive | Group | Residue Functionality |
|---|---|---|
| aryl axides | amine | R—NH—R" |
| acyl azides | amide | R—CO—NH—R" |
| azidiformates | carbamate | R—O—CO—NH—R" |
| sulfonyl azides | sulfonamide | R—$SO_2$—NH—R" |
| phosphoryl azides | phosphoramide | $(RO)_2PO$—NH—R" |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

Those skilled in the art, given the present description, will be able to identify and select suitable thermochemically reactive groups to provide for covalent immobilization of appropriately derivatized nucleic acid sequences. For example, an amino derivatized nucleic acid sequence will undergo a covalent coupling reaction with an activated ester such as a NOS ester to provide an amide linking group. Similar activated esters such p-nitrophenyl and pentafluorophenyl esters would also provide amide links when reacted with amine groups. Those skilled in the art would also recognize numerous other amine-reactive functional groups such as isocyanates, thioisocyanates, carboxylic acid chlorides, epoxides, aldehydes, alkyl halides and sulfonate esters, such as mesylate, tosylate and tresylate, each of which could serve as the thermochemically reactive group.

In another example, the nucleic acid sequence can be derivatized with a sulfhydryl group using techniques well known in the art. The corresponding thermochemically reactive group would be, for example, a maleimide ring structure or an a-iodoacetamide. Either of these structures would react readily to provide a covalent linkage with the sulfhydryl derivatized nucleic acid sequence.

The functionalized polymers of this invention can be prepared by appropriate derivatization of a preformed polymer or, more preferably, by polymerization of a set of comonomers to give the desired substitution pattern. The latter approach is preferred because of the ease of changing the ratio of the various comonomers and by the ability to control the level of incorporation into the polymer. A combination of these two approaches can also be used to provide optimal structures.

In a preferred embodiment, for instance, monomers are prepared having a polymerizable group at one end of the molecule, separated by a spacer group from a photoreactive or thermochemically reactive group at the other end. For example, polymerizable vinyl groups such as acrylamides, acrylates, or maleimides can be coupled through a short hydrocarbon spacer to an activated ester such as a NOS ester or to a photoreactive group such as a substituted benzophenone. These compounds can be prepared and purified using organic synthesis techniques well known to those skilled in the art. Some of desired monomers are commercially available, such as MAPTAC, N-[3-(dimethylamino)propyl] methacrylamide (DMAPMA), and N-(3-aminopropyl) methacrylamide hydrochloride (APMA), these compounds providing quaternary ammonium salts, tertiary amines, and primary amines respectively along the backbone of the polymer.

Polymers and copolymers can be prepared from the above monomers as well, using techniques known to those skilled in the art. Preferably, these monomers and copolymers undergo free radical polymerization of vinyl groups using azo initiators such as 2,2'-azobisisobutyronitrile (AIBN) or peroxides such as benzoyl peroxide. The monomers selected for the polymerization are chosen based on the nature of the final polymer product. For example, a photoreactive polymer containing a NOS group is prepared from a monomer containing the photoreactive group and a second monomer containing the activated NOS ester.

The composition of the final polymer can be controlled by mole ratio of the monomers charged to the polymerization reaction. Typically these functionalized monomers are used at relatively low mole percentages of the total monomer content of the polymerization reaction with the remainder of the composition consisting of a monomer which is neither photoreactive nor thermochemically reactive toward the nucleic acid sequence. Examples of such monomers include, but are not limited to, acrylamide and N-vinylpyrrolidone. Based on the relative reactivities of the monomers used, the distribution of the monomers along the backbone is largely random.

In some cases, the thermochemically reactive group on the backbone of the polymer can itself act as a polymerizable monomer, if present during polymerization, thus requiring the introduction of that group in a second step following the initial formation of the polymer. For example, the preparation of a photoreactive polymer having maleimide along the backbone can be accomplished by an initial preparation of a polymer containing both photoreactive groups and amine groups using the techniques described above, followed by reaction of the amine groups with a heterobifunctional molecule containing a maleimide group and an isocyanate connected by a short hydrocarbon spacer. A wide variety of such polymer modification techniques are available using typical organic reactions known to those skilled in the art.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight. Structures of the various "Compounds" identified throughout these Examples can be found in Table 13 included below. NMR analyses were run on a 80 Mhz spectrometer unless otherwise stated.

EXAMPLES

Example 1

Preparation of 4-Benzoylbenzoyl Chloride (BBA-Cl) (Compound I)

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene:hexane to give 988 g (91 % yield) after drying in a vacuum oven. Product melting point was 92–94° C. Nuclear magnetic resonance (NMR) analysis at 80 MHz ($^1$H NMR (CDCl$_3$)) was consistent with the desired product: aromatic protons 7.20–8.25 (m, 9H). All chemical shift values are in ppm downfield from a tetramethylsilane internal standard. The final compound was stored for use in the preparation of a monomer used in the synthesis of photoactivatable polymers as described, for instance, in Example 3.

Example 2

Preparation of N-(3-Aminopropyl)methacrylamide Hydrochloride (APMA) (Compound II)

A solution of 1,3-diaminopropane, 1910 g (25.77 moles), in 1000 ml of CH$_2$Cl$_2$ was added to a 12 liter Morton flask and cooled on an ice bath. A solution of t-butyl phenyl carbonate, 1000 g (5.15 moles), in 250 ml of CH$_2$Cl$_2$ was then added dropwise at a rate which kept the reaction temperature below 15° C. Following the addition, the mixture was warmed to room temperature and stirred 2 hours. The reaction mixture was diluted with 900 ml of CH$_2$Cl$_2$ and 500 g of ice, followed by the slow addition of 2500 ml of 2.2 N NaOH. After testing to insure the solution was basic, the product was transferred to a separatory funnel and the organic layer was removed and set aside as extract #1. The aqueous was then extracted with 3×1250 ml of CH$_2$Cl$_2$, keeping each extraction as a separate fraction. The four organic extracts were then washed successively with a single 1250 ml portion of 0.6 N NaOH beginning with fraction #1 and proceeding through fraction #4. This wash procedure was repeated a second time with a fresh 1250 ml portion of 0.6 N NaOH. The organic extracts were then combined and dried over Na$_2$SO$_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of CHCl$_3$ was placed in a 12 liter Morton flask equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of CHCl$_3$. The rate of addition was controlled to keep the reaction temperature below 10° C. at all times. After the addition was complete, the ice bath was removed and the mixture was left to stir overnight. The product was diluted with 2400 ml of water and transferred to a separatory finnel. After thorough mixing, the aqueous layer was removed and the organic layer was washed with 2400 ml of 2 N NaOH, insuring that the aqueous layer was basic. The organic layer was then dried over Na$_2$SO$_4$ and filtered to remove drying agent. A portion of the CHCl$_3$ solvent was removed under reduced pressure until the combined weight of the product and solvent was approximately 3000 g. The desired product was then precipitated by slow addition of 11.0 liters of hexane to the stirred CHCl$_3$ solution, followed by overnight storage at 4° C. The product was isolated by filtration and the solid was rinsed twice with a solvent combination of 900 ml of hexane and 150 ml of CHCl$_3$. Thorough drying of the solid gave 900 g of N-[N'-(t-butyloxycarbonyl)-3-aminopropyl]-methacrylamide, m.p. 85.8° C. by DSC. Analysis on an NMR spectrometer was consistent with the desired product:

$^1$H NMR (CDCl$_3$) amide NH's 6.30–6.80, 4.55–5.10 (m, 2H), vinyl protons 5.65, 5.20 (m, 2H), methylenes adjacent to N 2.90–3.45 (m, 4H), methyl 1.95 (m, 3H), remaining methylene 1.50–1.90 (m, 2H), and t-butyl 1.40 (s, 9H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5 M by titration with 1 N NaOH using phenolphthalein as an indicator. The N-[N'-(t-butyloxycarbonyl)-3-aminopropyl] methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5 M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. Compound II was isolated by filtration and was dried to constant weight, giving a yield of 630 g with a melting point of 124.7° C. by DSC. Analysis on an NMR spectrometer was consistent with the desired product: $^1$H NMR (D$_2$O) vinyl protons 5.60, 5.30 (m, 2H), methylene adjacent to amide N 3.30 (t, 2H), methylene adjacent to amine N 2.95 (t, 2H), methyl 1.90 (m, 3H), and remaining methylene 1.65–2.10 (m, 2H). The final compound was stored for use in the preparation of a monomer used in the synthesis of photoactivatable polymers as described, for instance, in Example 3.

Example 3

Preparation of N-[3-(4-Benzoylbenzamido)propyl] methacrylamide (BBA-APMA) (Compound III)

Compound II 120 g (0.672 moles), prepared according to the general method described in Example 2, was added to a dry 2 liter, three-neck round bottom flask equipped with an overhead stirrer. Phenothiazine, 23–25 mg, was added as an inhibitor, followed by 800 ml of chloroform. The suspension was cooled below 10° C. on an ice bath and 172.5 g (0.705 moles) of Compound I, prepared according to the general method described in Example 1, were added as a solid. Triethylamine, 207 ml (1.485 moles), in 50 ml of chloroform was then added dropwise over a 1–1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from 4:1 toluene: chloroform using 23–25 mg of phenothiazine in each recrystallization to prevent polymerization. Typical yields of Compound III were 90% with a melting point of 147–151° C. Analysis on an NMR spectrometer was consistent with the desired product: $^1$H NMR (CDCl$_3$) aromatic protons 7.20–7.95 (m, 9H), amide NH 6.55 (broad t, 1H), vinyl protons 5.65, 5.25 (m, 2H), methylene adjacent to amide N's 3.20–3.60 (m, 4H), methyl 1.95 (s, 3H), and remaining methylene 1.50–2.00 (m, 2H). The final compound was stored for use in the synthesis of photoactivatable polymers as described, for instance, in Examples 9–11.

Example 4

Preparation of N-Succinimidyl 6-Maleimidohexanoate (MAL-EAC-NOS) (Compound IV)

A functionalized monomer was prepared in the following manner, and was used as described in Examples 9 and 12 to introduce activated ester groups on the backbone of a polymer. 6-Aminohexanoic acid, 100 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. After drying, the typical yield of the (Z)-4-oxo-5-aza-2-undecendioic acid was 158–165 g (90–95%) with a melting point of 160–165° C. Analysis on an NMR spectrometer was consistent with the desired product: $^1$H NMR (DMSO-d$_6$) amide proton 8.65–9.05 (m, 1H), vinyl protons 6.10, 6.30 (d, 2H), methylene adjacent to nitrogen 2.85–3.25 (m, 2H), methylene adjacent to carbonyl 2.15 (t, 2H), and remaining methylenes 1.00–1.75 (m, 6H).

(Z)-4-Oxo-5-aza-2-undecendioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to <60° C. and poured into a solution of 250 ml of 12 N HCl in 3 liters of water. The mixture was stirred 3 hours at room temperature and then was filtered through a filtration pad (Celite 545, J. T. Baker, Jackson, Tenn.) to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from 2:1 hexane:chloroform to give typical yields of 76–83 g (55–60%) with a melting point of 81–85° C. Analysis on a NMR spectrometer was consistent with the desired product: $^1$H NMR (CDCl$_3$) maleimide protons 6.55 (s, 2H), methylene adjacent to nitrogen 3.40 (t, 2H), methylene adjacent to carbonyl 2.30 (t, 2H), and remaining methylenes 1.05–1.85 (m, 6H).

The 6-maleimidohexanoic acid, 20.0 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12 g (0.104 mol) of N-hydroxysuccinimide and 16 ml (0.114 mol) of triethylamine. After stirring overnight at room temperature, the product was washed with 4×100 ml of water and dried over sodium sulfate. Removal of solvent gave 24 g of product (82%) which was used without further purification. Analysis on an NMR spectrometer was consistent with the desired product: $^1$H NMR (CDCl$_3$) maleimide protons 6.60 (s, 2H), methylene adjacent to nitrogen 3.45 (t, 2H), succinimidyl protons 2.80 (s, 4H), methylene adjacent to carbonyl 2.55 (t, 2H), and remaining methylenes 1.15–2.00 (m, 6H). The final compound was stored for use

Example 5

Preparation of N-Succinimidyl 6-Methacrylamidohexanoate (MA-EAC-NOS) (Compound V)

A functionalized monomer was prepared in the following manner, and was used as described in Example 11 to introduce activated ester groups on the backbone of a polymer. 6-Aminocaproic acid, 4.00 g (30.5 mmol), was placed in a dry round bottom flask equipped with a drying tube. Methacrylic anhydride, 5.16 g ( 33.5 mmol), was then added and the mixture was stirred at room temperature for four hours. The resulting thick oil was triturated three times with hexane and the remaining oil was dissolved in chloroform, followed by drying over sodium sulfate. After filtration and evaporation, a portion of the product was purified by silica gel flash chromatography using a 10% methanol in chloroform solvent system. The appropriate fractions were combined, 1 mg of phenothiazine was added, and the solvent was removed under reduced pressure. Analysis on an NMR spectrometer was consistent with the desired product: $^1$H NMR (CDCl$_3$) carboxylic acid proton 7.80–8.20 (b, 1H), amide proton 5.80–6.25 (b, 1H), vinyl protons 5.20 and 5.50 (m, 2H), methylene adjacent to nitrogen 3.00–3.45 (m, 2H), methylene adjacent to carbonyl 2.30 (t, 2H), methyl group 1.95 (m, 3H), and remaining methylenes 1.10–1.90 (m, 6H).

6-Methacrylamidohexanoic acid, 3.03 g (15.2 mmol), was dissolved in 30 ml of dry chloroform, followed by the addition of 1.92 g (16.7 mmol) of N-hydroxysuccinimide and 6.26 g (30.4 mmol) of 1,3-dicyclohexylcarbodiimide. The reaction was stirred under a dry atmosphere overnight at room temperature. The solid was then removed by filtration and a portion was purified by silica gel flash chromatography. Non-polar impurities were removed using a chloroform solvent, followed by elution of the desired product using a 10% tetrahydrofuran in chloroform solvent. The appropriate fractions were pooled, 0.2 mg of phenothiazine were added, and the solvent was evaporated under reduced pressure. This product, containing small amounts of 1,3-dicyclohexylurea as an impurity, was used without further purification. Analysis on an NMR spectrometer was consistent with the desired product: $^1$H NMR (CDCl$_3$) amide proton 5.60–6.10 (b, 1H), vinyl protons 5.20 and 5.50 (m, 2H), methylene adjacent to nitrogen 3.05–3.40 (m, 2H), succinimidyl protons 2.80 (s, 4H), methylene adjacent to carbonyl 2.55 (t, 2H), methyl 1.90 (m, 3H), and remaining methylenes 1.10–1.90 (m, 6H). The final compound was stored for use in the synthesis of photoactivatable polymers as described, for instance, in Example 11.

Example 6

Preparation of 4-Bromomethylbenzophenone (BMBP)(Compound VI)

4-Methylbenzophenone, 750 g (3.82 moles), was added to a 5 liter Morton flask equipped with an overhead stirrer and dissolved in 2850 ml of benzene. The solution was then heated to reflux, followed by the dropwise addition of 610 g (3.82 moles) of bromine in 330 ml of benzene. The addition rate was approximately 1.5 ml/min and the flask was illuminated with a 90 watt (90 joule/sec) halogen spotlight to initiate the reaction . A timer was used with the lamp to provide a 10% duty cycle (on 5 seconds, off 40 seconds), followed in one hour by a 20% duty cycle (on 10 seconds, off 40 seconds). At the end of the addition, the product was analyzed by gas chromatography and was found to contain 71% of the desired Compound VI, 8% of the dibromo product, and 20% unreacted 4-methylbenzophenone. After cooling, the reaction mixture was washed with 10 g of sodium bisulfite in 100 ml of water, followed by washing with 3×200 ml of water. The product was dried over sodium sulfate and recrystallized twice from 1:3 toluene:hexane. After drying under vacuum, 635 g of Compound VI were isolated, providing a yield of 60% and having a melting point of 112–114° C. Analysis on an NMR spectrometer was consistent with the desired product: $^1$H NMR (CDCl$_3$) aromatic protons 7.20–7.80 (m, 9H) and benzylic protons 4.48 (s, 2H). The final compound was stored for use in the preparation of a photoactivatable chain transfer agent as described in Example 7.

Example 7

Preparation of N-(2-Mercaptoethyl)-3,5-bis(4-benzoylbenzyloxy)benzamide (Compound VII)

3,5-Dihydroxybenzoic acid, 46.2 g (0.30 mol), was weighed into a 250 ml flask equipped with a Soxhlet extractor and condenser. Methanol, 48.6 ml, and concentrated sulfuric acid, 0.8 ml, were added to the flask and 48 g of 3A molecular sieves were placed in the Soxhlet extractor. The extractor was filled with methanol and the mixture was heated at reflux overnight. Gas chromatographic analysis of the resulting product showed a 98% conversion to the desired methyl ester. The solvent was removed under reduced pressure to give approximately 59 g of crude product. The product was used in the following step without further purification. A small sample was previously purified for NMR analysis, resulting in a spectrum consistent with the desired product: $^1$H NMR (DMSO-d$_6$) aromatic protons 6.75 (d, 2H) and 6.38 (t, 1H), and methyl ester 3.75 (s, 3H).

The entire methyl ester product from above was placed in a 2 liter flask with an overhead stirrer and condenser, followed by the addition of 173.25 g (0.63 mol) of Compound VI, prepared according to the general method described in Example 6, 207 g (1.50 mol) of potassium carbonate, and 1200 ml of acetone. The resulting mixture was then refluxed overnight to give complete reaction as indicated by thin layer chromatography (TLC). The solids were removed by filtration and the acetone was evaporated under reduced pressure to give 49 g of crude product. The solids were diluted with 1 liter of water and extracted with 3×1 liter of chloroform. The extracts were combined with the acetone soluble fraction and dried over sodium sulfate, yielding 177 g of crude product. The product was recrystallized from acetonitrile to give 150.2 g of a white solid, a 90% yield for the first two steps. Melting point of the product was 131.5° C. (DSC) and analysis on an NMR spectrometer was consistent with the desired product: 1H NMR (CDCl$_3$) aromatic protons 7.25–7.80 (m, 18H), 7.15 (d, 2H), and 6.70 (t, 1H), benzylic protons 5.05 (s, 4H), and methyl ester 3.85 (s, 3H).

The methyl 3,5-bis(4-benzoylbenzyloxy)benzoate, 60.05 g (0.108 mol), was placed in a 2 liter flask, followed by the addition of 120 ml of water, 480 ml of methanol, and 6.48 g (0.162 mol) of sodium hydroxide. The mixture was heated at reflux for three hours to complete hydrolysis of the ester. After cooling, the methanol was removed under reduced pressure and the sodium salt of the acid was dissolved in 2400 ml of warm water. The acid was precipitated using concentrated hydrochloric acid, filtered, washed with water, and dried in a vacuum oven to give 58.2 g of a white solid (99% yield). Melting point on the product was 188.3° C. (DSC) and analysis on an NMR spectrometer was consistent with the desired product: 1H NMR (DMSO-d6) aromatic protons 7.30–7.80 (m, 18H), 7.15 (d, 2H), and 6.90 (t, 1H), and benzylic protons 5.22 (s, 4H).

The 3,5-bis(4-benzoylbenzyloxy)benzoic acid, 20.0 g (36.86 mmol), was added to a 250 ml flask, followed by 36 ml of toluene, 5.4 ml (74.0 mmol) of thionyl chloride, and 28 μl of N,N-dimethylformamide. The mixture was refluxed for four hours to form the acid chloride. After cooling, the solvent and excess thionyl chloride were removed under reduced pressure. Residual thionyl chloride was removed by four additional evaporations using 20 ml of chloroform each. The crude material was recrystallized from toluene to give 18.45 g of product, an 89% yield. Melting point on the product was 126.9° C. (DSC) and analysis on an NMR spectrometer was consistent with the desired product: $^1$H NMR (CDCl$_3$) aromatic protons 7.30–7.80 (m, 18H), 7.25 (d, 2H), and 6.85 (t, 1H), and benzylic protons 5.10 (s, 4H).

The 2-aminoethanethiol hydrochloride, 4.19 g (36.7 mmol), was added to a 250 ml flask equipped with an overhead stirrer, followed by 15 ml of chloroform and 10.64 ml (76.5 mmol) of triethylamine. After cooling the amine solution on an ice bath, a solution of 3,5-bis(4-benzoylbenzyloxy)benzoyl chloride, 18.4 g (32.8 mmol), in 50 ml of chloroform was added dropwise over a 50 minute period. Cooling on ice was continued 30 minutes, followed by warming to room temperature for two hours. The product was diluted with 150 ml of chloroform and washed with 5×250 ml of 0.1 N hydrochloric acid. The product was dried over sodium sulfate and recrystallized twice from 15:1 toluene: hexane to give 13.3 g of product, a 67% yield. Melting point on the product was 115.9° C. (DSC) and analysis on an NMR spectrometer was consistent with the desired product.: 1H NMR (DMSO-d$_6$) aromatic protons 7.20–7.80 (m, 18H), 6.98 (d, 2H), and 6.65 (t, 1H), amide NH 6.55 (broad t, 1H), benzylic protons 5.10 (s, 4H), methylene adjacent to amide N 3.52 (q, 2H), methylene adjacent to SH 2.10 (q, 2H), and SH 1.38 (t, 1H). The final compound was stored for use as a chain transfer agent in the synthesis of photoactivatable polymers as described, for instance, in Example 12.

Example 8

Preparation of N-Succinimidyl 11 -(4-Benzoylbenzamido)undecanoate (BBA-AUD-NOS) (Compound VIII)

Compound I (50 g, 0.204 mol), prepared according to the general method described in Example 1, was dissolved in 2500 ml of chloroform, followed by the addition of a solution of 43.1 g (0.214 mol) of 11-aminoundecanoic acid and 60.0 g (1.5 mol) of sodium hydroxide in 1500 ml of water. The mixture was stirred vigorously for one hour in a 5 liter Morton flask to insure thorough mixing of the two layers. The mixture was acidified with 250 ml of concentrated hydrochloric acid and stirred an additional 30 minutes. The organic layer was separated and the aqueous was extracted with 3×500 ml of chloroform. The combined organic extracts were dried over sodium sulfate, filtered, and evaporated to give a solid. The product was recrystallized from toluene to give 68.37 g (82%) of 11-(4-benzoylbenzamido)undecanoic acid with a melting point of 107–109° C. Analysis on an NMR spectrometer was consistent with the desired product: $^1$H NMR (CDCl$_3$) aromatic protons 7.20–7.80 (m, 9H), amide NH 6.30 (broad t, 1H), methylene adjacent to amide N 3.35 (m, 2H), methylene adjacent to carbonyl 2.25 (t, 2H), and remaining methylenes 1.00–1.80 (m, 16H).

The 11-(4-benzoylbenzamido)undecanoic acid, 60.0 g (0.146 mol), was dissolved with warming in 1200 ml of anhydrous 1,4-dioxane in an oven-dried 2000 ml flask. After cooling to room temperature, 17.7 g ( 0.154 mol) of N-hydroxysuccinimide and 33.2 g (0.161 mol) of 1,3-dicyclohexylcarbodiimide were added to the solution and the mixture was stirred overnight under a dry atmosphere. The solids were then removed by filtration, rinsing the filter cake with 1,4-dioxane. The solvent was then removed under vacuum and the product was recrystallized twice from ethanol. After thorough drying in a vacuum oven, 53.89 g (73 % yield) of a white solid were obtained with a melting point of 97–99° C. Analysis on an NMR spectrometer was consistent with the desired product: $^1$H NMR (CDCl$_3$) aromatic protons 7.20–7.80 (m, 9H), amide NH 6.25 (broad t, 1H), methylene adjacent to amide N 3.35 (m, 2H), methylenes on succinimidyl ring 2.75 (s, 4H), methylene adjacent to carbonyl 2.55 (t, 2H), and remaining methylenes 1.00–1.90 (m, 16H).

Example 9

Preparation of Copolymer of Acrylamide. BBA-APMA. and MAL-EAC-NOS (Random Photo PA-PolyNOS) (Compounds IX, A-D)

A photoactivatable copolymer of the present invention was prepared in the following manner. Acrylamide, 4.298 g (60.5 mmol), was dissolved in 57.8 ml of tetrahydrofuran (THF), followed by 0.219 g ( 0.63 mmol) of Compound III, prepared according to the general method described in Example 3, 0.483 g (1.57 mmol) of Compound IV, prepared according to the general method described in Example 4, 0.058 ml (0.39 mmol) of N,N,N',N'-tetramethylethylenediamine (TEMED), and 0.154 g (0.94 mmol) of 2,2'-azobisisobutyronitrile (AIBN). The solution was deoxygenated with a helium sparge for 3 minutes, followed by an argon sparge for an additional 3 minutes. The sealed vessel was then heated overnight at 60° C. to complete the polymerization. The solid product was isolated by filtration and the filter cake was rinsed thoroughly with THF and CHCl$_3$. The product was dried in a vacuum oven at 30° C. to give 5.34 g of a white solid. NMR analysis (DMSO-d$_6$) confirmed the presence of the NOS group at 2.75 ppm and the photogroup load was determined to be 0.118 mmol BBA/g of polymer. The MAL-EAC-NOS composed 2.5 mole % of the polymerizable monomers in this reaction to give Compound IX-A.

The above procedure was used to prepare a polymer having 5 mole % Compound IV. Acrylamide, 3.849 g (54.1 mmol), was dissolved in 52.9 ml of THF, followed by 0.213 g ( 0.61 mmol) of Compound VI, prepared according to the general method described in Example 3, 0.938 g (3.04 mmol) of Compound IV, prepared according to the general method described in Example 4, 0.053 ml (0.35 mmol) of TEMED and 0.142 g (0.86 mmol) of AIBN. The resulting solid, Compound IX-B, when isolated as described above, gave 4.935 g of product with a photogroup load of 0.101 mmol BBA/g of polymer.

The above procedure was used to prepare a polymer having 10 mole % Compound IV. Acrylamide, 3.241 g (45.6 mmol), was dissolved in 46.4 ml of THF, followed by 0.179 g ( 0.51 mmol) of Compound III, prepared according to the general method described in Example 3, 1.579 g (5.12 mmol) of Compound IV, prepared according to the general method described in Example 4, 0.047 ml (0.31 mmol) of TEMED and 0.126 g (0.77 mmol) of AIBN. The resulting solid, Compound IX-C, when isolated as described above, gave 4.758 g of product with a photogroup load of 0.098 mmol BBA/g of polymer.

A procedure similar to the above procedure was used to prepare a polymer having 2.5 mole % Compound IV and 2 mole % Compound III. Acrylamide, 16.43 g (231.5 mmol); Compound III, prepared according to the general method described in Example 3, 1.70 g (4.85 immol); Compound IV, prepared according to the general method described in Example 4, 1.87 g (6.06 mmol); and THF (222 ml) were stirred in a round bottom flask with an argon sparge at room temperature for 15 minutes. TEMED, 0.24 ml (2.14 mmol), and AIBN, 0.58 g (3.51 mmol), were added to the reaction. The reaction was then refluxed for 4 hours under an atmosphere of argon. The resulting solid, Compound IX-D, when isolated as described above, gave 19.4 g of product with a photogroup load of 0.23 mmol BBA/g of polymer.

Example 10

Preparation of Copolymer of Acrylamide, BBA-APMA, and [3-(Methacryloylamino)propyl] trimethylammonium Chloride (Random Photo PA-PolyQuat) (Compounds X, A-B)

A photoactivatable copolymer of the present invention was prepared in the following manner. Acrylamide, 10.681 g (0.150 mol), was dissolved in 150 ml of dimethylsulfoxide (DMSO), followed by 0.592 g (1.69 mmol) of Compound III, prepared according to the general method described in Example 3, 3.727 g (16.90 mmol) of [3-(methacryloylamino)propyl]trimethylammonium chloride (MAPTAC), delivered as 7.08 ml of a 50% aqueous solution, 0.169 ml (1.12 mmol) of TEMED and 0.333 g (2.03 mmol) of AIBN. The solution was deoxygenated with a helium sparge for 4 minutes, followed by an argon sparge for an additional 4 minutes. The sealed vessel was then heated overnight at 55° C. to complete the polymerization. The DMSO solution was diluted with water and dialyzed against deionized water using 12,000–14,000 molecular weight cutoff tubing. Lyophilization of the resulting solution gave 14.21 g of a white solid. NMR analysis ($D_2O$) confirmed the presence of the methyl groups on the quaternary ammonium groups at 3.10 ppm and the photogroup load was determined to be 0.101 mmol BBA/g of polymer. The Compound III constituted 1 mole % of the polymerizable monomer in this reaction to give Compound X-A.

The above procedure was used to prepare a polymer having 2 mole % of Compound III. Acrylamide, 10.237 g (0.144 mol), was dissolved in 145 ml of DMSO, followed by 1.148 g (3.277 mmol) of Compound III, prepared according to the general method described in Example 3, 3.807 g (17.24 mmol) of MAPTAC, delivered as 7.23 ml of a 50% aqueous solution, 0.164 ml (1.09 mmol) of TEMED and 0.322 g (1.96 mmol) of AIBN. Workup as described above gave 12.54 g of product (Compound X-B) with a photogroup load of 0.176 mmol BBA/g of polymer.

Example 11

Preparation of Copolymer of Acrylamide, BBA-APMA, MA-EAC-NOS, and [3-(Methacryloylamino)propyl]trimethylammonium Chloride (Random Photo PA-PolyNOS-Poly Quat) (Compound XI)

A photoactivatable copolymer of the present invention was prepared in the following manner. The water in the commercially available 50% aqueous MAPTAC was removed by azeotropic distillation with chloroform. The aqueous MAPTAC solution, 20 ml containing 10.88 g of MAPTAC, was diluted with 20 ml of DMSO and 100 ml of chloroform. This mixture was refluxed into a heavier-than-water liquid-liquid extractor containing anhydrous sodium sulfate for a total of 80 minutes. A slow flow of air was maintained during the reflux to inhibit polymerization of the monomer. At the end of the reflux, the excess chloroform was removed under reduced pressure to leave a DMSO solution of MAPTAC at an approximate concentration of 352 mg/ml.

Acrylamide, 1.7 g (23.90 mmol), was dissolved in 57.7 ml of dimethylsulfoxide (DMSO), followed by 0.215 g (0.614 mmol) of Compound III, prepared according to the general 1[] method described in Example 3, 1.93 ml (0.677 g, 3.067 mmol) of the above MAPTAC/DMSO solution, 0.91 g (3.068 mmol) of Compound V, prepared according to the general method described in Example 5, and 0.060 g (0.365 mmol) of AIBN. The solution was deoxygenated with a helium sparge for 4 minutes, followed by an argon sparge for an additional 4 minutes. The sealed vessel was then heated overnight at 55° C. to complete the polymerization. The polymer was isolated by pouring the reaction mixture into 600 ml of diethyl ether. The solids were separated by centrifuging and the product was washed with 200 ml of diethyl ether and 200 ml of chloroform. Evaporation of solvent under vacuum gave 3.278 g of product with a photoload of 0.185 mmol BBA/g of polymer.

Example 12

Copolymer of Acrylamide and MAL-EAC-NOS using N-(2-Mercaptoethyl)-3,5-bis(4-benzoylbenzyloxy)benzamide (End-point Diphoto PA-PolyNOS) (Compound XII)

A photoactivatable copolymer of the present invention was prepared in the following manner. Acrylamide, 3.16 g (44.5 mrol), was dissolved in 45.0 ml of tetrahydrofuran, followed by 0.164 g (1 mmol) of AIBN, 0.045 ml (0.30 mmol) of TEMED, 0.301 g (0.5 mmol) of Compound VII, prepared according to the general method in Example 7, and 1.539 g (5 mmol) of Compound IV, prepared according to the general method described in Example 4. The solution was deoxygenated with a helium sparge for 4 minutes, followed by an argon sparge for an additional 4 minutes. The sealed vessel was then heated overnight at 55° C. to complete the polymerization. The precipitated polymer was isolated by filtration and was washed with chloroform. The final product was dried in a vacuum oven to provide 4.727 g of polymer having a photogroup load of 0.011 mmol BBA/g of polymer.

Example 13

Copolymer of N-[3-(Dimethylamino)propyl] methacrylamide and BBA-APMA (Random Photo Poly Tertiary Amine) (Compound XIII)

A photoactivatable copolymer of the present invention was prepared in the following manner. N-[3-(Dimethylamino)propyl]methacrylamide, 33.93 g (0.2 mol), was dissolved in 273 ml of DMSO, followed by 16.6 ml of concentrated HCl and 6.071 g (17.3 mmol) of Compound III, prepared according to the general method described in Example 3. Finally, 0.29 ml (1.93 nmmol) of TEMED, 0.426 g (2.6 mmol) of AIBN, and 100 ml of water were added to the reaction mixture. The solution was deoxygenated with a helium sparge for 10 minutes and the head space was then filled with argon. The sealed vessel was heated overnight at 55° C. to complete the polymerization. The product was then dialyzed against deionized water for several days using 12,000–14,000 MWCO tubing. The product was filtered following dialysis to remove any solids and was lyophilized to give 47.27 g of a solid product. The polymer was determined to have a photoload of 0.33 mmol BBA/g of polymer.

Example 14

Preparation of N-succinimidyl 5-oxo-6-aza-8-nonenoate (Allyl-GLU-NOS) (Compound XIV)

A functional monomer was prepared in the following manner, and was used in Example 15 to introduce activated ester groups on the backbone of the polymer. Glutaric anhydride, 20 g (0.175 mole), was dissolved in 100 ml chloroform. The glutaric anhydride solution was cooled to <10° C using an ice bath. Allyl amine, 10 g (0.177 mole), was dissolved in 50 ml chloroform and added to the cooled solution of glutaric anhydride with stirring. The addition rate of allyl amine was adjusted to keep the reaction temperature <10° C. After the allyl amine addition was completed, the reaction solution was allowed to come to room temperature while stirring overnight. After removing the solvent, the 5-oxo-6-aza-8-nonenoic acid isolated amounted to 31.4g (105% crude) with a dual DSC melting point of 35.1° C and 44.9° C. NMR analysis at 300 MHz was consistent with the desired product: 1H NMR (CDCl$_3$) amide proton 6.19 (b, 1H), vinyl protons 5.13, 5.81 (m, 3H), methylene adjacent to amide N 3.85 (m, 2H), methylenes adjacent to carbonyls 2.29, 2.39 (t, 4H), and central methylene 1.9. (m, 2H).

The 5-oxo-6-aza-8-nonenoic acid, 20.54 g (0.12 mole), N-hydroxysuccinimide (NHS), 15.19 g (0.13 mole), and 204 ml dioxane were placed in a 1 L 3-necked round bottom flask equipped with an overhead stirrer and an addition funnel. Dicyclohexylcarbodiimide ("DCC"), 29.7 g (0.144 mole), was dissolved in 50 ml dioxane and placed in the addition funnel. The DCC solution was added with stirring to the acid/NHS solution over 20 minutes, and the resulting mixture was allowed to stir at room temperature overnight. The reaction mixture was filtered on a Buchner finnel to remove dicyclohexylurea (DCU). The solid was washed with 2×100 ml dioxane. The solvent was evaporated to give 41.37 g residue, which was washed with 4×75 ml hexane. After the solvents were removed, the yield of crude NOS ester was 41.19 g. One recrystallization of the crude NOS product from toluene gave a 60% yield with a DSC melting point of 90.1° C. NMR analysis at 300 MHz was consistent with the desired product: $^1$H NMR (CDCl$_3$) amide proton 6.02 (b, 1H), vinyl protons 5.13, 5.80 (m, 3H), methylene adjacent to amide N 3.88 (m, 2H), succinimidyl protons 2.83 (s, 4H), methylenes adjacent to carbonyls 2.31, 2.68 (t, 4H), and central methylene 2.08 (m, 2H). The final compound was stored for use in the synthesis of photoactivatable polymers as described in Example 15.

Example 15

Preparation of Copolymer of Vinylpyrrolidinone, BBA-APMA, and Allyl-GLU-NOS (Random Photo PVP-PolyNOS)(Compound XV)

A photoactivatable copolymer of the present invention was prepared in the following manner. Vinylpyrrolidinone, 4.30 g (38.73 mmol), was dissolved in 5.2 ml of DMSO along with 0.14 g (0.41 mmol) of Compound III, prepared according to the general method described in Example 3, 0.55 g (2.06 mmol) Compound XIV, prepared according to the general method described in Example 14, by combining 0.08 g (0.49 mmol) of AIBN and 0.005 ml (0.033 mmol) of TEMED. The solution was deoxygenated with a helium sparge for 3 minutes. The head space was replaced with argon, and the vessel was sealed for an overnight heating at 55° C. The viscous solution was diluted with 15 ml chloroform, and then precipitated by pouring into 200 ml diethyl ether. The precipitate was dissolved in 15 ml chloroform, and precipitated a second time in 200 ml ether. The product was dried in a vacuum oven at 30° C. to give 4.79 g of a white solid. NMR analysis (CDCl$_3$) confirmed the presence of the NOS group at 2.81 ppm and the photogroup load was determined to be 1.1 mmol BBA/g of polymer. The Allyl-GLU-NOS composed 5.0 mole % of the polymerizable monomers in this reaction to give Compound XV.

Example 16

Comparison of Random Photo PA-PolyNOS (Compound IX-C) with Random Photo PA-PolyNOS-PolyQuat (Compound XI) on Polystyrene (PS) Microwell Plates Compound IX-C and Compound XI were separately dissolved in deionized water at 5 mg/ml. The PS plates (PS, Medium Bind, Corning Costar, Cambridge, MA) containing 100 μl of Compound IX-C and Compound XI in separate wells were illuminated with a Dymax lamp (model no. PC-2, Dymax Corporation, Torrington, Conn.) which contained a Heraeus bulb (W. C. Heraeus GmbH, Hanau, Federal Republic of Germany). The illumination duration was for 1.5 minutes at a intensity of 1–2mW/cm$^2$ in the wavelength range of 330–340 rm. The coating solution was then discarded and the wells were air dried for two hours. The plates were then illuminated for an additional one minute. The coated plates were used immediately to immobilize oligonucleotides stored in a sealed pouch for up to 2 months.

The 50 base oligomer (-mer) capture probe 5'-NH$_2$-GTCTGAGTCGGAGCCAGGGCGGCCGCCAACAGC AGGAGCAGCGTGCACGG-3' (SEQ ID NO:1) (synthesized with a 5'-amino-modifier containing a C-12 spacer) at 10 pmoles/well was incubated in PS wells in 50 mM phosphate buffer, pH 8.5, 1 mM EDTA at 37° C. for one hour. The hybridization was performed as follows using the complementary 5'-Biotin-CCGTGCACGCTGCTCCTGCTGTTGGCG-GCCGCCCTGGCTCCGACTC AGAC -3'(SEQ ID NO:3) detection probe or non-complementary 5'-Biotin-CGGTGGATGGAGCAGGAGGGGCCC GAGTATTGG-GAGCGGGAGACA CAGAA-3' (SEQ ID NO:4) oligo, both of which were synthesized with a 5'-biotin modification.

The plates with immobilized capture probe were washed with phosphate buffered saline (PBS, 10 mM Na$_2$PO$_4$, 150 mM NaCl, pH 7.2) containing 0.05% Tween 20 using a Microplate Auto Washer (model EL 403H, Bio-Tek Instruments, Winooski, Vt.). The plates were then blocked at 55° C. for 30 minutes with hybridization buffer, which consisted of 5X SCC (0.75 M NaCl, 0.075 M citrate, pH 7.0), 0.1% lauroylsarcosine, 1% casein, and 0.02% sodium dodecyl sulfate. When the detection probe was hybridized to the capture probe, 50 fmole of detection probe in 100 μl were added per well and incubated for one hour at 55° C. The plates were then washed with 2X SSC containing 0.1% sodium dodecyl sulfate for 5 minutes at 55° C. The bound detection probe was assayed by adding 100 μl of a conjugate of streptavidin and horseradish peroxidase (SA-HRP, Pierce, Rockford, Ill.) at 0.5 μg/ml and incubating for 30 minutes at 37° C. The plates were then washed with PBS/Tween, followed by the addition of peroxidase substrate (H$_2$O$_2$ and tetramethylbenzidine, Kirkegard and Perry Laboratories, Gaithersburg, Md.) and measurement at 655 nm on a microwell plate reader (model 3550, Bio-Rad Labs, Cambridge, Mass.). The plates were read at 10 minutes.

The results listed in Table 1 indicate that microwell plates coated with Compound IX-C did not effectively immobilize amine-derivatized capture probes. However, by comparison Compound XI, as a coating, provided significant binding and good hybridization signals. Compound IX-C reagent most likely passivated the surfaces and prevented the association of capture oligos. In contrast when Compound XI was used, the oligonucleotide was attracted to the surface by ionic interactions where it could then be covalently bonded with the NOS groups.

TABLE 1

Hybridization Signals (A$_{655}$) from PS Microwell Plates Coated with Compound IX-C and Compound XI.

| | Compound IX-C | Compound XI |
|---|---|---|
| Complementary Detection Probe | 0.187 ± 0.031 | 1.666 ± 0.064 |

TABLE 1-continued

Hybridization Signals ($A_{655}$) from PS Microwell Plates Coated with Compound IX-C and Compound XI.

|  | Compound IX-C | Compound XI |
|---|---|---|
| Non-complementary Detection Probe | 0.127 ± 0.016 | 0.174 ± 0.005 |

Example 17

Coating of Various Microwell Plates with a Mixture of Random Photo PA-PolyNOS (Compound IX-B) and Random Photo PA-PolyQuat (Compound X-B)

A coating solution containing a mixture of 5 mg/ml of Compound IX-B and 0.5 mg/ml of Compound X-B was prepared in deionized water. This mixture was used to treat polypropylene (PP, Coming Costar, Cambridge, Mass.), PS, polycarbonate (PC, Coming Costar, Cambridge, Mass.) and polyvinyl chloride (PVC, Dynatech, Chantilly, Va.) multi-wells as described in Example 16. A 30-mer capture oligonucleotide 5'-NH$_2$-GTCTGAGTCGGAGCCAGGGCGGCCGCCAAC-3' (SEQ ID NO:2), (synthesized with a 5'-amino-modifier containing a C-12 spacer) at 0.03, 0.1, 0.3, 1, 3, or 10 pmole/well was incubated at 4° C. overnight. The hybridization was performed as previously described in Example 16 using complementary SEQ ID NO:3 detection oligonucleotide or non-complementary SEQ ID NO:4 oligo. Since PP plates are not optically transparent, the contents of each well were transferred to PS wells after a 20 minute incubation with the chromogenic substrate. The hybridization signals were measured in the PS plates. The other plates were read without transferring at 10 minutes. Signal levels are only comparable within the same substrate group due to the different geometries of microwell plates made from different materials. Table 2 lists the hybridization signals and shows the relationship between the intensity of the hybridization signals and the amount of capture probe applied to various microwell plates coated with a mixture of Compound IX-B and Compound X-B. On PP and PVC plates, adsorption of probes was very low and the coatings with the polymeric reagents improved the signals dramatically. The signal increased with increasing capture probe added to the coated wells, but leveled off at approximately 3 pmole/well capture. The plateau in the amount of signal generated was not due to a saturating level of hybridization, but rather to the limits of the color change reaction in the calorimetric assay.

Oligonucleotide derivatives adsorb efficiently onto uncoated PS and PC microwell plates and result in specific hybridization signals. Cros et al. (U.S. Pat. No. 5,510,084) also reported that amine-functionalized oligonucleotides adsorbed satisfactorily onto polystyrene microwell plates by unknown mechanisms. However, there is marked variability in the amount of adsorption on uncoated PS plates among different lots (Chevier et al. *FEMS* 10:245, 1995).

TABLE 2

Hybridization Signals ($A_{655}$) From Various Microwell Plate Materials Coated With a Mixture of Compound IX-B and Compound X-B

| | Capture Oligonucleotide Added (pmole/well) | | | | | | | | | | | |
|---|---|---|---|---|---|---|---|---|---|---|---|---|
| | 0.03 | | 0.1 | | 0.3 | | 1 | | 3 | | 10 | |
| | Comp | NC | Comp | NC | Comp | NC | Comp | NC | Comp | NC | Comp | NC |
| PP | | | | | | | | | | | | |
| Uncoated | 0.083 | 0.082 | 0.076 | 0.072 | 0.076 | 0.074 | 0.088 | 0.074 | 0.070 | 0.067 | 0.078 | 0.073 |
| Coated | 0.541 | 0.099 | 1.070 | 0.099 | 1.769 | 0.091 | 2.283 | 0.094 | 2.582 | 0.141 | 2.490 | 0.320 |
| PVC | | | | | | | | | | | | |
| Uncoated | 0.074 | 0.079 | 0.081 | 0.075 | 0.097 | 0.078 | 0.137 | 0.076 | 0.215 | 0.081 | 0.337 | 0.092 |
| Coated | 0.423 | 0.116 | 0.875 | 0.110 | 1.326 | 0.112 | 1.583 | 0.142 | 1.628 | 0.186 | 1.604 | 0.332 |
| PS | | | | | | | | | | | | |
| Uncoated | 0.235 | 0.099 | 0.435 | 0.091 | 0.827 | 0.090 | 1.205 | 0.093 | 1.380 | 0.093 | 1.404 | 0.136 |
| Coated | 0.435 | 0.121 | 0.801 | 0.105 | 1.177 | 0.116 | 1.401 | 0.132 | 1.470 | 0.132 | 1.487 | 0.302 |
| PC | | | | | | | | | | | | |
| Uncoated | 0.676 | 0.248 | 1.364 | 0.244 | 2.103 | 0.256 | 2.701 | 0.266 | 2.745 | 0.295 | 2.930 | 0.388 |
| Coated | 1.034 | 0.327 | 1.602 | 0.306 | 2.136 | 0.295 | 2.218 | 0.287 | 2.380 | 0.342 | 2.500 | 0.572 |

Comp.: Complementary detection probe was added for hybridization.
NC: Non-complementary detection probe was added for hybridization.

Example 18

Evaluation of End-point Diphoto PA-polyNOS (Compound XII) and Random Photo PA-PolyQuat (Compound X-B) on PP and PVC Microwell Plates A coating solution containing a mixture of 5 mg/ml of Compound XII and 0.5 mg/ml of Compound X-B was prepared with deionized water. This mixture of the two reagents was used to coat PP and PVC microwell plates under conditions comparable to those described in Example 16. The 30-mer SEQ ID NO:2 capture oligonucleotide at 0.03, 0.1, 0.3, 1, 3, or 10 pmole/well in 0.1 ml was incubated at 4° C. overnight. The hybridization was performed as described in Example 16 using complementary SEQ ID NO:3 detection oligonucleotide or non-complementary SEQ ID NO: 4 oligonucleotide. The hybridization signals listed in Table 3 demonstrate the relationship between the intensity of the hybridization signals and the amount of capture probe applied to PP and PVC microwell plates coated with a mixture of Compound XII and Compound X-B. The signal increased with increasing capture oligonucleotides added to the coated wells, but leveled off at approximately 1 pmole/well. The signal-to-noise ratio (from complementary vs. non-complementary detection probes) was as high as 26 and 11 for coated PP and PVC surfaces, respectively.

TABLE 3

Hybridization Signals ($A_{655}$) From PP and PVC Plates Coated With Mixture of Compound XII and Compound X-B.

| pmole/well Capture Added | PP Microwell plates | | PVC Microwell plates | |
| --- | --- | --- | --- | --- |
| | Comp. Detection | Non-comp. | Comp. Detection | Non-comp. |
| 0.03 | 0.153 ± 0.008 | 0.070 ± 0.007 | 0.289 ± 0.029 | 0.094 ± 0.020 |
| 0.1 | 0.537 ± 0.042 | 0.075 ± 0.009 | 0.759 ± 0.054 | 0.104 ± 0.014 |
| 0.3 | 1.206 ± 0.106 | 0.080 ± 0.003 | 1.262 ± 0.023 | 0.117 ± 0.011 |
| 1 | 2.157 ± 0.142 | 0.081 ± 0.003 | 1.520 ± 0.044 | 0.189 ± 0.064 |
| 3 | 2.624 ± 0.162 | 0.108 ± 0.012 | 1.571 ± 0.031 | 0.179 ± 0.016 |
| 10 | 2.921 ± 0.026 | 0.200 ± 0.018 | 1.625 ± 0.040 | 0.286 ± 0.021 |

Example 19

Sequential Coating with Random Photo PA-PolyQuat (Compound X-B) and BBA-AUD-NOS (Compound VIII)

Compound X-B at 0.1 mg/ml in deionized water was incubated in PP and PVC wells for 20 minutes. The plates were illuminated as previously described in Example 16 with the solution in the wells for 1.5 minutes. The solution was discarded and the wells were dried. Compound VIII at 0.5 mg/ml in isopropyl alcohol (IPA) was incubated in the Compound X-B coated wells for 5 minutes. The solution was then removed, the plate dried and illuminated as described in Example 16 for one minute after the wells were dried. The 30-mer SEQ ID NO:2 capture oligonucleotide at 0.03, 0.1, 0.3, 1, 3, or 10 pmole/well in 0.1 ml was incubated at 4° C. overnight. The hybridization was performed as described in Example 16 using complementary (SEQ ID NO:3) detection oligonucleotide or non-complementary SEQ ID NO:4 oligo. Table 4 contains the hybridization signals and shows the relationship between the intensity of the hybridization signals and the amount of capture probe applied to PP and PVC microwell plates coated with Compound X-B followed by Compound VIII coating. The signal increased with increasing capture probe added to the coated wells, but leveled off at approximately 1 pmole/well capture oligo. The signals were up to 29- and 11- fold higher for coated PP and PVC surfaces, respectively, as compared to the uncoated controls.

TABLE 4

Hybridization Signals ($A_{655}$) From PP and PVC Microwell Plates Coated With Compound X-B Followed by Compound VIII Coating.

| pmole/well | PP Microwell plates | | PVC Microwell plates | |
| --- | --- | --- | --- | --- |
| Capture Added | Uncoated | Coated | Uncoated | Coated |
| 0.03 | 0.083 ± 0.003 | 0.157 ± 0.004 | 0.074 ± 0.004 | 0.244 ± 0.014 |
| 0.1 | 0.076 ± 0.003 | 0.544 ± 0.006 | 0.081 ± 0.005 | 0.694 ± 0.065 |
| 0.3 | 0.076 ± 0.006 | 1.095 ± 0.015 | 0.097 ± 0.010 | 1.113 ± 0.033 |
| 1 | 0.088 ± 0.006 | 1.676 ± 0.030 | 0.137 ± 0.016 | 1.304 ± 0.027 |
| 3 | 0.070 ± 0.010 | 1.865 ± 0.057 | 0.215 ± 0.023 | 1.237 ± 0.013 |
| 10 | 0.078 ± 0.009 | 2.274 ± 0.005 | 0.337 ± 0.024 | 1.182 ± 0.041 |

Example 20

Comparision of Random Photo PA-PolyQuat (Compound X-A) with a Mixture of Random Photo PA-PolyNOS (Compound IX-A) and Random Photo PA-PolyQuat (Compound X-A)

Compound X-A at 0.5 or 0.1 mg/ml was incubated in PP microwell plates for 10 minutes. The plates were then illuminated as described in Example 16. A coating solution containing a mixture of Compound IX-A and Compound X-A was prepared at two ratios, 5/0.5 mg/ml and 0.5/0.1 mg/ml of Compound IX-A/Compound X-A in deionized water to coat PP microwell plates. The solution was incubated in the wells for 10 minutes and the wells were illuminated as described in Example 16. The 30-mer SEQ ID NO:2 capture oligonucleotide at 1 pmole/well was incubated in each well at 37° C. for one hour. The hybridization was done as described in Example 16 using complementary SEQ ID NO:3 detection oligonucleotide or non-complementary SEQ ID NO:4 oligo. The results listed in Table 5 indicate that the coating containing the combination of Compound IX-A and Compound X-A gave higher signals as compared to those from Compound X-A coating alone.

TABLE 5

Hybridization Signals ($A_{655}$) From Compound X-A Coated PP Microwell Plates.

| Ratio of Compound IX-A/Compound X-A (mg/ml) | Comp. Detection | Non-comp. Detection |
| --- | --- | --- |
| 5/0.5 | 1.436 ± 0.056 | 0.077 ± 0.001 |
| 0/0.5 | 0.454 ± 0.149 | 0.052 ± 0.006 |
| 0.5/0.1 | 1.346 ± 0.044 | 0.062 ± 0.003 |
| 0/0.1 | 0.192 ± 0.082 | 0.055 ± 0.002 |

Example 21

Comparision of Non-modified Oligonucleotide vs. Amine-Modified Oligonucleotide on Random Photo PA-PolyNOS (Compound IX-B) and Random Photo PA-PolyQuat (Compound X-B) on Coated Microwell Plates A coating solution containing a mixture of Compound IX-B (5 mg/ml) and Compound X-B (0.5 mg/ml) was prepared in deionized water to coat PP, PS and PVC microwell plates. The solution was incubated for approximately 10 minutes and illuminated as described in Example 16. The 30-mer capture 5'-$NH_2$-TTCTGTGTCTCC CGCTCCCAATACTCGGGC-3'(SEQ ID NO:5) oligonucleotide at 1 pmole/well was coupled to the wells in 50 MM phosphate buffer, pH 8.5, 1 mM EDTA at 4° C. overnight. The hybridization was performed as described in Example 16 using complementary detection oligonucleotide SEQ ID NO:4 or non-complementary oligonucleotide (SEQ ID NO:3). To determine the effect of the amine-functionality of the capture oligo, a non-modified 30-mer capture probe 5'-TTCTGTGTCTCC CGCTCCCAATACTCGGGC-3' (SEQ ID NO:6) (with no amine) was also added to the coated surfaces and tested. The results shown in Table 6 indicate that when an oligonucleotide without the 5'-amine modification was used as the capture probe on Compound IX-B/Compound X-B coated surfaces, the hybridization signal was less than 30% of that with amine modification.

buffer without the SEQ ID NO:3 probe. After washing three times with 2X SSC containing 0.1% SDS for 5 minutes at 550 C and three times with PBS/0.05% Tween, the plates were cut into individual wells and dissolved in tetrahydrofuran. The amount of radioactivity in each well was measured by scintillation counting in Aquasol-2 Fluor (DuPont NEN, Boston, Mass.). The results in Table 7 show that both Compound IX-A and Compound X-A were required to give good immobilization of capture probe. Also, increasing the concentrations of Compound IX-A and Compound X-A increased the amount of the capture oligonucleotide immobilized. At the highest concentrations tested, the signal to noise ratio was greater than 3000 to 1.

TABLE 6

Signals ($A_{655}$) Generated From Hybridization Reactions With Either SEQ ID NO:5 or SEQ ID NO:6 Oligonucleotides on Compound IX-B/Compound X-B Coated Microwell Plates.

| | No Capture Added | | Non-modified Capture | | Amine-modified Capture | |
|---|---|---|---|---|---|---|
| | Comp. Detection | Non-comp. Detection | Comp. Detection | Non-comp. Detection | Comp. Detection | Non-comp. Detection |
| PP | | | | | | |
| Uncoated | 0.032 ± 0.001 | 0.036 ± 0.004 | 0.033 ± 0.001 | 0.036 ± 0.001 | 0.037 ± 0.005 | 0.033 ± 0.001 |
| Coated | 0.038 ± 0.002 | 0.040 ± 0.001 | 0.555 ± 0.041 | 0.044 ± 0.001 | 1.915 ± 0.029 | 0.066 ± 0.003 |
| PVC | | | | | | |
| Uncoated | 0.248 ± 0.049 | 0.176 ± 0.008 | 0.259 ± 0.049 | 0.128 ± 0.013 | 0.404 ± 0.100 | 0.118 ± 0.025 |
| Coated | 0.115 ± 0.027 | 0.090 ± 0.014 | 0.379 ± 0.028 | 0.091 ± 0.014 | 1.319 ± 0.027 | 0.101 ± 0.017 |
| PS | | | | | | |
| Uncoated | 0.084 ± 0.013 | 0.089 ± 0.014 | 0.668 ± 0.047 | 0.085 ± 0.023 | 1.269 ± 0.034 | 0.106 ± 0.024 |
| Coated | 0.080 ± 0.006 | 0.081 ± 0.023 | 0.364 ± 0.010 | 0.089 ± 0.015 | 1.437 ± 0.012 | 0.098 ± 0.005 |

Example 22

Oligonucleotide Loading Densities on Microwell Plates Coated with Random Photo PA-PolyNOS (Compound IX-A) and Random Photo PA-PolyQuat (Compound X-A)

Radiolabeled assays were performed to determine oligonucleotide loading densities and to verify results from the colorimetric assay system. In this Example, combination coatings of Compound IX-A and Compound X-A were performed on PVC wells as described in Example 16. The SEQ ID NO:2 and SEQ ID NO:5 30-mer capture oligonucleotides were immobilized on coated wells. A radiolabeled SEQ ID NO:2 probe was used to determine the loading density of immobilized capture oligonucleotides on the well surface. A radiolabeled SEQ ID NO:3 detection probe, which was complementary to SEQ ID NO:2, but not to SEQ ID NO:5, was used to measure hybridization reactions of the immobilized capture probes. Oligonucleotides SEQ ID NO:2 and SEQ ID NO:3 were radiolabeled at the 3'-end using terminal transferase (Boehringer Mannheim, Indianapolis, Ind.) and $\alpha$-$^{32}$P-ddATP (3000 Ci/mmole, Amersham, Arlington Heights, Ill.) according to the manufacturer's specifications. $^{32}$P-labeled SEQ ID NO:2 and unlabeled SEQ ID NO:2 and SEQ ID NO:5 capture probes were incubated in coated wells at 50 pmole/well for 2.25 hours at room temperature. The plates were washed and blocked as in Example 16.

The wells with the unlabeled capture probes were hybridized with the $^{32}$P-labeled SEQ ID NO:3 detection probe in hybridization buffer for 1 hour at 55° C. Wells containing the $^{32}$P-labeled capture probe were incubated in hybridization

TABLE 7

Densities of Immobilized Capture Oligonucleotide and Hybridized $^{32}$P-Detection Oligo.

| Mixture of Coating Reagents | | Immobilized | Hybridized comp. | Hybridized non-comp. |
|---|---|---|---|---|
| Compound IX-A (mg/ml) | Compound X-A (mg/ml) | capture fmole/well | detection fmole/well | detection fmole/well |
| 0 | 0 | 41.3 | 2.3 | 0.6 |
| 0 | 0.05 | 37.5 | 10.9 | 0.7 |
| 0.55 | 0 | 32.6 | 5.4 | 0.6 |
| 1 | 0.1 | 344.1 | 308.8 | 26.4 |
| 0.1 | 0.1 | 285.7 | 222.2 | 55.7 |
| 1 | 0.001 | 52.8 | 26.2 | 0.6 |
| 0.1 | 0.001 | 73.5 | 20.8 | 13.1 |
| 1.19 | 0.05 | 280.4 | 256.9 | 1.1 |
| 0.55 | 0.12 | 401.9 | 379.1 | 0.7 |
| 0.55 | 0.05 | 338.0 | 315.1 | 1.6 |
| 2 | 0.5 | 1633.4 | 1108.4 | 0.3 |

Example 23

Comparison between Random Photo-Polytertiary Amine (Compound XIII), Random Photo-PA-PolyNOS (Compound IX-A) and a Mixture of Random Photo PA-PolyNOS (Compound IX-A) and Random Photo-Polytertiary Amine (Compound XIII)

Compound XIII at 0.02 mg/ml in deionized water was incubated in PP microwell plates for 10 minutes. The wells were illuminated as described in Example 16. Compound IX-A was coated on PP wells at 2 mg/ml in deionized water as described for Compound XIII. A coating solution containing a mixture of 2 mg/ml Compound IX-A and 0.02 mg/ml Compound XIII in deionized water was prepared and coated as described for Compound XIII. The 30-mer SEQ ID NO:2 capture oligonucleotide at 5 pmole/well was incubated in each well at 37° C. for one hour. The hybridization was done as described in Example 16 using complementary SEQ ID NO:3 detection oligonucleotide and non-complementary SEQ ID NO:4 oligonucleotide. The contents of each well were transferred to PS wells after a 10 minute incubation with the peroxidase substrate. The results listed in Table 8 indicate that the combination of Compound IX-A and Compound XIII gave higher signals compared to those from Compound IX-A or Compound XIII coating alone.

TABLE 8

Hybridization Signals ($A_{655}$) From Coated PP Microwell Plates.

| Coating | Comp. Detection | Non-comp. Detection |
|---|---|---|
| Compound IX-A | 0.057 ± 0.001 | 0.052 ± 0.006 |
| Compound XIII | 0.746 ± 0.042 | 0.081 ± 0.009 |
| Compound IX-A/Compound XIII Mixture | 1.195 ± 0.046 | 0.078 ± 0.014 |

Example 24

Nucleic Acid Sequence Immobilization on an Amine Derivatized Surface

A copolymer of the present invention is prepared in the following manner. Acrylamide, 5.686 g (80.0 mmol), is dissolved in 100 ml of DMSO, followed by the addition of 3.083 g (10.0 mmol) of Compound IV, prepared according to the general method described in Example 4, and 2.207 g (10.0 mmol) of MAPTAC, delivered as a dry DMSO solution prepared according to the general method described in Example 11. TEMED, 0.134 ml (0.89 mmol), and AIBN, 0.197 g (1.20 mmol), are added to the mixture and the system is deoxygenated with a helium sparge for 5 minutes, followed by an argon sparge for an additional 5 minutes. The sealed vessel is heated at 55° C. to complete the polymerization. The polymer is isolated by pouring the reaction mixture into 800 ml of diethyl ether and centrifuging to separate the solids. The product is washed with 200 ml of diethyl ether, followed by 200 ml of chloroform. The polymer is dried under vacuum to remove remaining solvent.

A polymer surface is derivatized by plasma treatment using a 3:1 mixture of methane and ammonia gases. (See, e.g., the general method described in U.S. Pat. No. 5,643, 580). A mixture of methane (490 SCCM) and ammonia (161 SCCM) are introduced into the plasma chamber along with the polymer part to be coated. The gases are maintained at a pressure of 0.2–0.3 torr and a 300–500 watt glow discharge is established within the chamber. The sample is treated for a total of 3–5 minutes under these conditions. Formation of an amine derivatized surface is verified by a reduction in the water contact angle compared to the uncoated surface.

The amine derivatized surface is incubated for 10 minutes at room temperature with a 10 mg/ml solution of the above polymer in a 50 mM phosphate buffer, pH 8.5. Following this reaction time, the coating solution is removed and the surface is washed thoroughly with deionized water and dried thoroughly. Immobilization of oligomer capture probe and hybridization is performed as described in Example 16.

Example 25

Immobilization and Hybridization of Oligonucleotides on Photo-Polymeric NOS Coated Glass Slides—Comparison of coatings with and with out Photo PA PolyQuat (Compound X-A)

Soda lime glass microscope slides (Erie Scientific, Portsmouth, New Hampshire) were silane treated by dipping in a mixture of p-tolyldimethylchlorosilane (T-Silane) and N-decyldimethylchlorosilane (D-Silane, United Chemical Technologies, Bristol, Pennsylvania), 1% each in acetone, for 1 minute. After air drying, the slides were cured in an oven at 120° C. for one hour. The slides were then washed with acetone followed by DI water dipping. The slides were further dried in oven for 5–10 minutes.

Compound IX-A, IX-D, and XV at various concentrations and with or without Compound X-A, were sprayed onto the silane treated slide, which were then illuminated using a Dymax lamp (25 mjoule/$cm^2$ as measured at 335 nm with a 10 nm band pass filter on an International Light radiometer) while wet, washed with water, and dried. Oligonucleotides were printed on the slides using an X, Y, Z motion controller to position a 0.006" id blunt end needle filled with oligonucleotide solution. Two oligonucleotides were immobilized to the prepared slides. One containing an amine on the 3' end and Cy3 fluorescent tag (Amersham, Arlington Heights, Ill.) on the 5' end, 5' Cy3-GTCTGAGTCGGAGCCAGGGCGGCCGCCAAC-NH2-3'(SEQ ID NO:7) (amino modifier has a C12 spacer) and the other containing an amine on the 5' end, 5'-NH2-TTCTGTGTCTCCCGCTCCCAATACTCGGGC-3'(SEQ ID NO:5) ) (amino modifier has a C12 spacer). They were printed at a concentration of 8 pmole/ptl in 50 mM sodium phosphate pH 8.5 containing 10% sodium sulfate and 1 mM EDTA. Slides were placed overnight on a rack in a sealed container with saturated sodium chloride to maintain a relative humidity of 75%. Slides printed with (SEQ ID NO:7) were then washed for 5 minutes in PBS/0.05% Tween-20, for 90 minutes in blocking buffer (0.2 M Tris with 10 mM ethanolamine) at 500 C, and for 2 hours in wash buffer (5X SSC, 0.1% N-lauryl sarcosine, and 0.1% sodium dodecyl sulfate). Slides were washed twice with water and spun in a centrifuge to dry. They were than scanned using a General Scanning Scan-Array 3000 fluorescence scanner (Watertown, Massachusetts) and the average intensities of the resulting spots were measured. Slides printed with (SEQ ID NO:5) were washed for 5 minutes in PBS/0.05% Tween-20 and for 30 minutes in blocking buffer (0.2 M Tris with 10 mM ethanolamine) at 50° C. The slides were finally washed with water and dried in a centrifuge.

Fluorescently labeled complementary oligonucleotide, 5'-Cy3-CGGTGGATGGAGCAGGAGGGGCCCGAGTATTGG GAGCGGGAGACACAGAA-3'(SEQ ID NO:8), was hybridized to the slides by placing 10 Ill of hybridization solution (4X SSC, 0.1% N-laurylsarcosine, 2 mg/ml tRNA) on the slide and placing a cover slip on top. The slides were then kept at 50° C. high humidity (75%) to prevent drying out of the hybridization solution. Slides were then rinsed with 4X SSC, 2X SSC preheated to 50° C. for 2 minutes, 2X SSC for 2 minutes, and then twice into 0.1X SSC for 2 minutes each. Slides were spun dry in a centrifuge. They were then scanned using a General Scanning fluorescence scanner. Average intensities of the resulting spots and background levels were measured. The results listed in Table 9 show that the coatings without compound X-A immobilize slightly less oligonucleotide but hybridization of a fluorescent oligonucleotide results in slightly higher signal. The resulting background is less on coatings which do not contain compound X-A. It also shows that polymers containing PVP backbone compound (i.e. Compound XV) are effective at immobilizing DNA and give good hybridization results.

TABLE 9

Immobilization and Hybridization of Oligonucleotides to Glass Microscope Slides.

| Compound % BBA | % NOS | Poly-NOS conc g/l | Cmpd X-A conc g/l | immobilized SEQ ID NO:7 signal[1] | hybridization SEQ ID NO:8 signal[2] | bkg | S/N |
|---|---|---|---|---|---|---|---|
| Compound IX-A | | 1.25 | 0 | 39151 | 38512 | 45 | 856 |
| Compound IX-A | | 1 | 0.25 | 42598 | 35674 | 88 | 405 |
| Compound IX-A | | 2.5 | 0 | 35153 | 31061 | 34 | 914 |
| Compound IX-A | | 2 | 0.5 | 44233 | 24735 | 75 | 332 |
| Compound IX-D | | 1.25 | 0 | 30655 | 41669 | 45 | 926 |
| Compound IX-D | | 1 | 0.25 | 38594 | 34300 | 99 | 346 |
| Compound IX-D | | 2.5 | 0 | 41226 | 48976 | 67 | 736 |
| Compound IX-D | | 2 | 0.5 | 46444 | 22743 | 123 | 185 |
| Compound XV | | 1.25 | 0 | 28228 | 50248 | 34 | 1478 |
| Compound XV | | 1 | 0.25 | 31544 | 47321 | 97 | 488 |

[1]Laser power set at 60% and photomultiplier tube set at 60%
[2]Laser power set at 80% and photomultiplier tube set at 80%

Example 26

Hybridization of Immobilized PCR products on Coated Glass Slides with OligonucleotideDetection Probe. Comparison between Random Photo-PA-PolyNOS (Compound IX-A) and a Mixture of Random Photo-PA-PolyNOS (Compound IX-A) and Random Photo-PA-PolyQuat (Compound X-A).

Glass slides were coated with organosilane as described in Example 25. Compound IX-A at 1.25 mg/ml in water or a mixture of 1 mg/ml Compound IX-A and 0.25 mg/ml Compound X-A in water was coated onto silane treated glass slides as described in Example 25.

PCR products from β-galactosidase gene were custom prepared by ATG Laboratories, Inc. (Eden Prairie). Primer with 5'-amine modification on the sense strand and unmodified primer on the anti-sense strand were used to prepare double-stranded- PCR products at 0.5 and 1 kilobase (kb) pair length. The control DNAs without amine were also made. The DNAs at concentration 0.2 µg/µl in 80 mM sodium phosphate buffer, pH 8.5, and 8% sodium sulfate were printed on the activated slides using microarraying spotting pins from TeleChem International (San Jose, Calif.). The coupling was allow to proceed in a sealed container with 75% humidity overnight at room temperature.

To evaluate the signals from immobilized PCR products on microarrays, the slides were placed in boiling water for 2 minutes to denature double-stranded DNA and to remove the non-attached strand. The slides were then incubated with 50 mM ethanolamine in 0.1 M Tris buffer, pH 9 at 50° C. for 15 minutes to block residual reactive groups on the surfaces. The slides were then incubated with pre-hybridization solution under glass cover slips at 50° C. for 15 minutes to decrease the non-specific backgrounds. The pre-hybridization solution contained 5X SSC, 5X Denhardt's solution (0.1 mg/ml each of bovine serum albumin, Ficoll and PVP), 0.1 mg/ml salmon sperm DNA and 0.1% SDS. The hybridization was then performed with 20 fmole/µl of a fluorescent complementary detection oligo, 5'-Cy3-ACGCCGA GTTAACGCCATCA (SEQ ID NO9), in the pre-hybridization solution overnight at 45° C. Slides were then washed and the hybridization signals scanned as described in Example 25.

The results listed in Table 10 indicate that the glass slides coated with Compound IX-A and mixture of Compound IX-A/X-A had comparable signals. Amine-containing PCR product had at least 30-fold higher hybridization signals than non-modified DNA. The low level of signals with unmodified DNA was probably due to side reactions between amines on the heterocyclic bases to the activated surfaces.

TABLE 10

Hybridization Signals With Immobilized 0.5 Kb DNA And a Complementary Detection Oligonucleotide SEQ ID NO:9 on Compound IX-A/Compound X-A Coated Glass Slides.

| Coating | Amine-primer PCR product | Non-modified primer PCR product |
|---|---|---|
| Compound IX-A | 10,385 ± 2,379 | 341 ± 61 |
| Compound IX-A and Compound X-A Mixture | 16,858 ± 4,008 | 341 ± 79 |

Example 27

Hybridization of Immobilized PCR products on Coated Glass Slides with Oligonucleotide Detection Probe—Comparison between SurModics and other Commercial Slides.

PCR products from cDNA clones can be attached to the positively charged glass surfaces, such as polylysine; DeRisi, et. al., (Science, 278, 680–686, 1997), and a covalent approach having aldehyde groups has been reported by Schena (Schena et.al., Proc. Natl. Acad. Sci. USA, 93, 10614–10619). In this example PCR products were attached to those surfaces and the hybridization signals were compared with the coatings from this invention. SurModics glass slides were coated with mixture of Compound IX-A and Compound X-A as described in Example 25. Silylated glass slides that have reactive aldehyde groups for immobilizing amine-functionalized DNA was manufactured by CEL Associates, Inc. (Houston, Tex.). Polylysine glass slides were purchased from Sigma.

PCR products at 1 kb length from β-galactosidase at 1.5 pmole/µl in 50 mM sodium phosphate buffer, pH 8.5, 1 mM EDTA and 3% sodium sulfate were printed onto silylated slides, polylysine slides and SurModics coated slides using 0.006" id needle as described in Example 25. The SurModics slides were then incubated in 75% relative humidity chamber for 2 days, denatured by submerging in boiling water bath for 2 minutes, and blocked with 10 mM ethanolamine, 0.2 M Tris, pH 8.5 for 30 minutes at 50° C. The silylated slides were incubated in a humidified incubator for 4 hours and then reduced with sodium borohydride as suggested by the manufacturer. The polylysine slides were UV crosslinked and then blocked with succinic anhydride as described in the literature[1]. All the processed slides were hybridized with 20 finole/μl of complementary detection oligonucleotide SEQ ID NO:9 in 4X SSC, 2 mg/ml tRNA, 0.1 % lauroylsarcosine at 45° C. overnight. The slides were washed and hybridization signals were scanned as described in Example 25.

The results are shown in the following Table 11. There was no difference in signals between amine-modified versus unmodified DNA on silylated and polylysine slides. Only SurModics coatings demonstrated that specific attachment was due to having a 5'-amine on the PCR products. This provides evidence of end-point attachment of DNA up to 1 kb with SurModics coatings. Polylysine slides had the highest background probably due to ionic and/or inonspecific binding of the DNA onto the surfaces.

TABLE 11

Hybridization Signals With Immobilized 1 Kb DNA and a Complementary Detection Oligonucleotide SEQ ID NO:9 on Coated Glass Slides. Comparison of Compound IX-A/ Compound X-A Coated Slides and Commercial Glass Slides.

| Coating | Amine-primer PCR product | Non-modified primer PCR product | Background |
|---|---|---|---|
| Compound IX-A and Compound X-A Mixture | 26,580 ± 3,219 | 946 ± 185 | 88 |
| Silylated | 5,611 ± 2,063 | 7,050 ± 2,211 | 114 |
| Polylysine | 4,3674 ± 2,832 | 4,3206 ± 4,743 | 3,075 |

Example 28

Immobilization and Hybridization of PCR Products with cDNA Detection Probe on Photo-Polymeric NOS Coated Glass Slides.

Two sets of slides were prepared as described in Example 26. Three PCR product sequences (designated Fl 1, XEF, daf) containing an amine on both, the forward, the reverse or neither strand (provided by Axys Pharmaceuticals, La Jolla, Calif.) were dissolved in printing buffer (80ng/μl), heated at 100° C., cooled on ice, and printed on the slides using a Generation II Arrayer (Molecular Dynamics, Sunnyvale, California). After incubation overnight as described in Example 25, the slides were placed in a boiling water bath for 2 minutes, washed twice with PBS/0.05% tween-20, rinsed twice with water, and put in blocking buffer for 30 minutes at 50° C. The slides were than rinsed with water and spun dry. Slides were prehybridized as described in Example 26 and hybridized to a mixture of fluorescently (Cy3) labeled cDNA (provided by Axys Pharmaceuticals) in 50% formamide, 5X SSC, 0.1% SDS, and 0.1 mg/ml salmon sperm DNA at 42° C. overnight. This mixture contained complementary probes to the forward strand of all three PCR product targets. The Fl I probe was spiked at a 1 to 50,000 mass ratio relative to the other two sequences. After hybridization, the slides were washed and scanned as described in Example 25. The average intensities of the spots are shown in Table 12. Slides which were hybridized to a cDNA probe mixture which did not contain the F11 probe showed no signal in these spots. The results show that both coating types give comparable hybridization results. The coating containing compound X-A had much higher background. This was especially true in the area near where the PCR product was printed.

TABLE 12

Immobilization of PCR Products and Hybridization to Fluorescently Labeled cDNA on Glass Microscope Slides. Numbers are Fluorescent Signal[1].

| | | amine on | | | |
|---|---|---|---|---|---|
| coated with compound IX-A | | both strands | forward strand | reverse strand | neither strand |
| 0.85 Kb | XEF | 2664.5 | 6125.5 | 759.5 | 3590.5 |
| 1 Kb | daf | | 42921.5 | | 14294 |
| 1 Kb | F11 | 588 | 1859.5 | 123.5 | 891.5 | background = 80

| | | amine on | | | |
|---|---|---|---|---|---|
| coated with mixture compounds IX-A & X-A | | both strands | forward strand | reverse strand | neither strand |
| 0.85 Kb | XEF | 3001 | 12896 | 779 | 4119 |
| 1 Kb | daf | | 44132.5 | | 13269.5 |
| 1 Kb | F11 | 535 | 1687.5 | 133 | 860.5 | background = varies from 100 to 2500

[1]Laser power set at 80% and photomultiplier tube set at 80%

TABLE 13

Compounds.

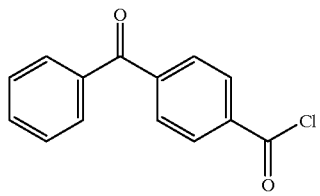

COMPOUND I

TABLE 13-continued
Compounds.
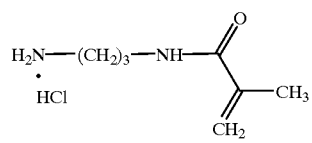
COMPOUND II
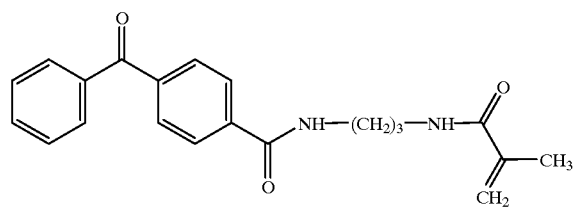
COMPOUND III
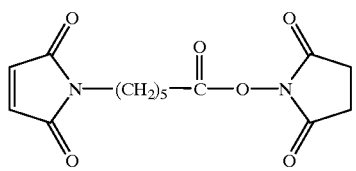
COMPOUND IV
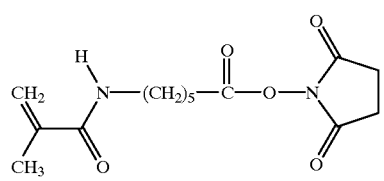
COMPOUND V
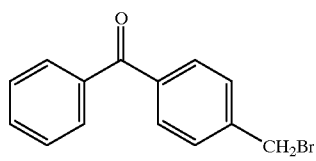
COMPOUND VI
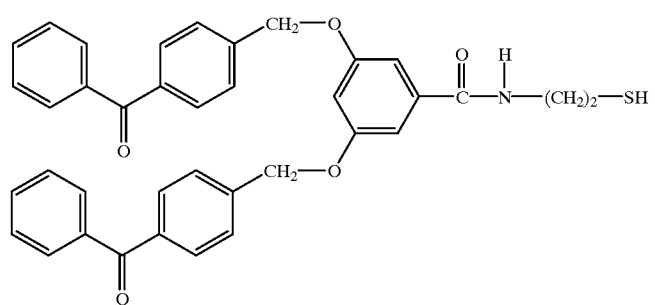
COMPOUND VII TABLE 13-continued
Compounds.
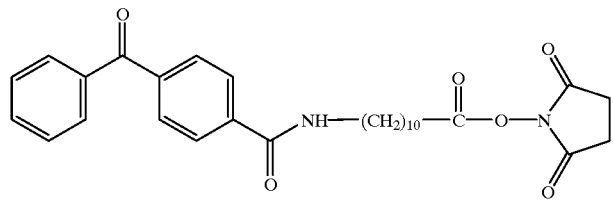
COMPOUND VIII
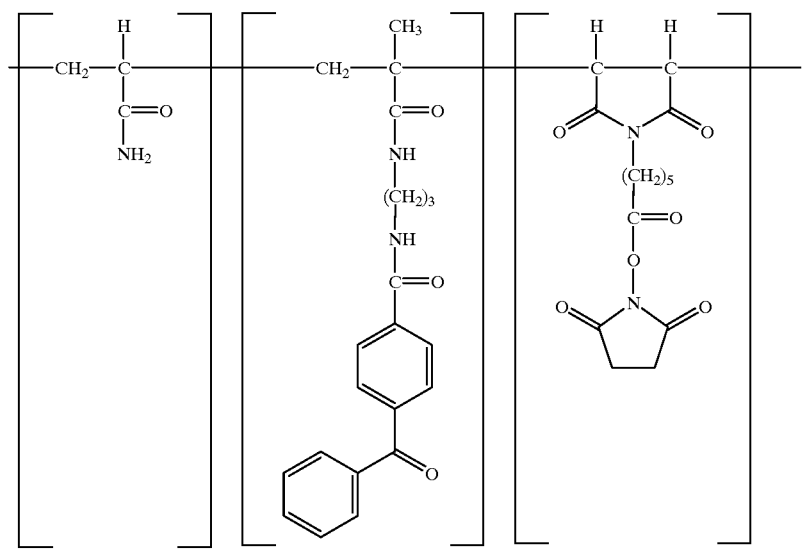
COMPOUND IX
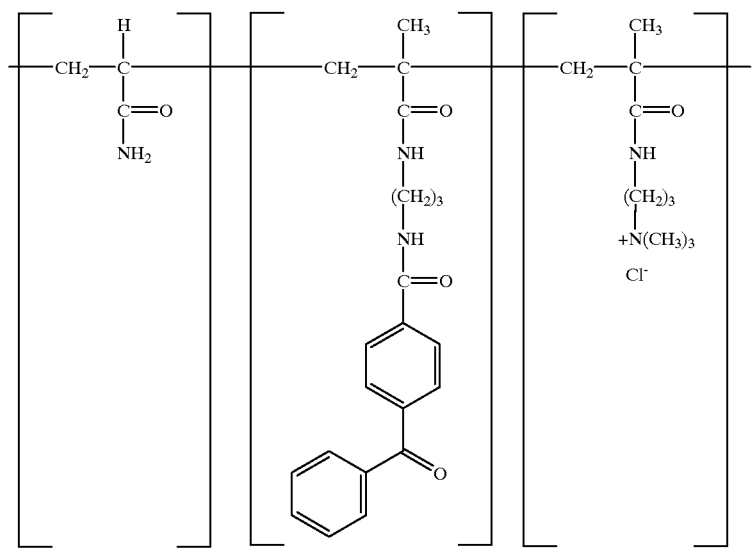
COMPOUND X TABLE 13-continued
Compounds.
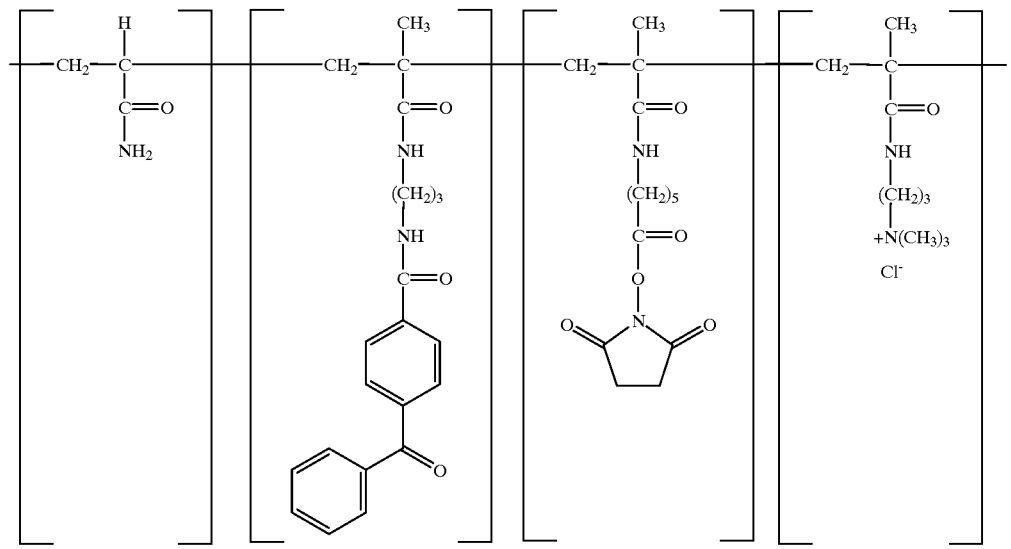
COMPOUND XI
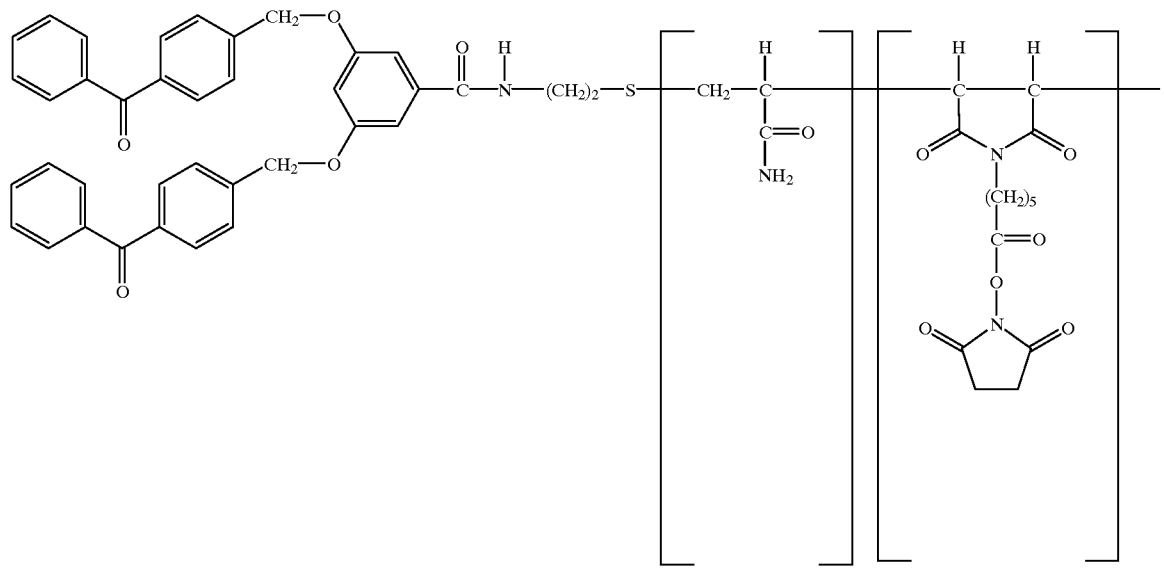
COMPOUND XII TABLE 13-continued
Compounds.
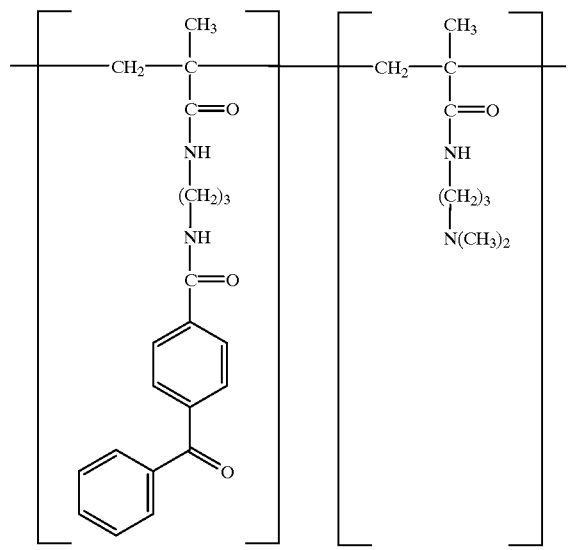
COMPOUND XIII
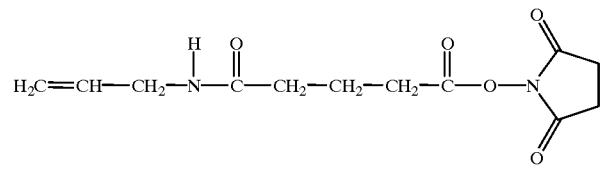
COMPOUND XIV
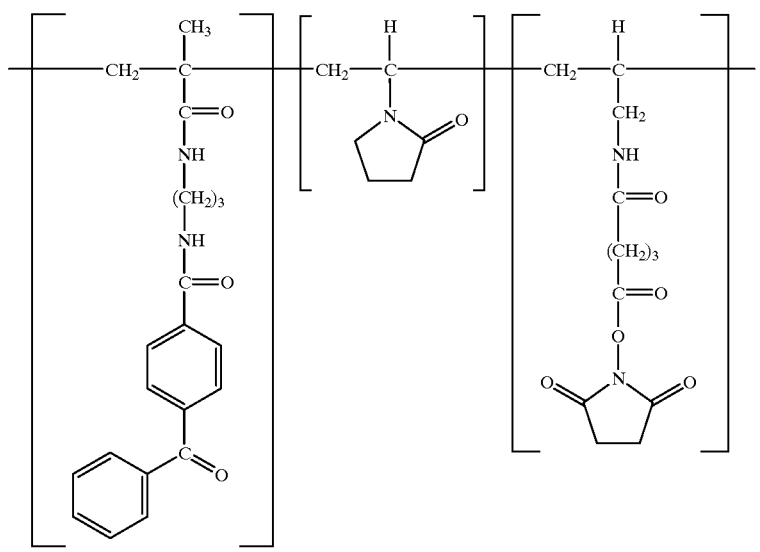
Compound XV

What is claimed is:

1. An activated slide comprising a support surface coated with a bound composition of a reagent composition, the bound composition comprising a polymeric backbone having more than one pendent thermochemically amine-reactive or sulfhydryl-reactive groups configured and arranged to form covalent bonds with fundamental groups on a target molecule, the reagent composition being coated and immobilized on the surface in a manner that permits: a) small sample volume of a solution containing the target molecule to be applied in the form of a discrete spot on the reagent composition-coated surface, b) target molecule present in the sample volume to become attached to the bound composition by reaction between the functional groups of the target molecule and the thermochemically amine-reactive or sulfhydryl-reactive groups of the bound composition, and c) substantially all unattached target molecule to be washed from the sport without undue detectable amounts of target molecule in the area surrounding the spot, and wherein the bound composition is configured and arranged to form covalent bonds with functional groups on the target molecule without the use of attracting groups to attract the target molecule to the bound composition.

2. An activated slide according to claim 1 wherein the activated slide is adapted for fabricating a microarray wherein the target molecule comprises a nucleic acid and the surface comprises the surface of a plastic, silicon hydride, or organosilane-pretreated glass or silicone slide.

3. An activated slide according to claim 2 wherein the nucleic acid comprises one or more functional groups selected from the group consisting of amine and sulfhydryl groups.

4. An activated slide according to claim 1 wherein the activated slide is configured and arranged to receive a sample in an amount of twenty nanoliters or less.

5. An activated slide according to claim 1 wherein the reagent composition comprises one or more latent reactive groups comprising photoreactive groups for attaching the reagent composition to the surface of the slide upon application of energy from a suitable source, wherein the latent reactive groups immobilize the composition onto the slide.

6. An activated slide according to claim 1 wherein the reagent composition comprises thermochemically reactive groups and photoreactive groups, wherein the thermochemically reactive groups and the photoreactive groups are pendent from the polymeric backbone and the photoreactive groups are selected from the group consisting of photoreactive aryl ketones.

7. An activated slide according to claim 6 wherein the photoreactive aryl ketones are each, independently, selected from the group consisting of acetophenone, benzophenone, anthraquinone, anthrone, and heterocyclic analogs of anthrone.

8. An activated slide according to claim 1 wherein the polymeric backbone is selected from the group consisting of acrylics, vinyls, nylons, polyurethanes and polyethers, the pendent thermochemically reactive groups are selected from the group consisting of activated esters, epoxides, azlactones, activated hydroxyls, aldehydes, isocyanates, thioisocyanates, carboxylic acid chlorides, alkyl halides, maleimide, and α-iodoacetamide, and the backbone further comprises one or more pendent photoreactive groups selected from the group consisting of aryl ketones.

9. An activated slide for binding target molecule in a sample, the slide comprising:

a. a support surface; and b. a bound composition attached to the support surface, wherein the bound composition comprises a polymeric backbone having more than one thermochemically amine-reactive or sulfhydryl-reactive groups attache thereto, and wherein the bound composition is configured and arranged to form covalent bonds with functional groups on the target molecule without use of attracting groups to attract the target molecule to the bound composition.

10. An activated slide according to claim 9 wherein the activated slide is adapted for fabricating a microarray wherein the target molecule comprises a nucleic acid and the surface comprises the surface of a plastic, silicon hydride, or organosilane-pretreated glass or silicone slide.

11. An activated slide according to claim 10 wherein the nucleic acid comprises one or more functional groups selected from the group consisting of amine and sulfhydryl groups.

12. An activated slide according to claim 9 wherein the activated slide is configured and arranged to receive a sample in an amount of twenty nanoliters or less.

13. An activated slide according to claim 9 wherein the bound composition comprises a reaction product of a reagent composition with the surface, wherein the reagent composition comprises one or more photoreactive groups for attaching the reagent composition to the surface of the slide upon application of energy from a suitable source, wherein the photoreactive groups immobilize the reagent composition onto the slide to form the bound composition.

14. An activated slide according to claim 13 wherein the reagent composition comprises thermochemically reactive groups and photoreactive groups, wherein the thermochemically reactive and photoreactive groups are pendent from one or more hydrophilic polymeric backbones and the photoreactive groups are photoreactive aryl ketones.

15. An activated slide according to claim 14 wherein the photoreactive aryl ketones are each, independently, selected from the group consisting of acetophenone, benzophenone, anthraquinone, anthrone, and heterocyclic analogs of anthrone.

16. An activated slide according to claim 9 wherein the polymeric backbone is selected from the group consisting acrylics, vinyls, nylons, polyurethanes and polyethers, the pendent thermochemically reactive groups are selected from the group consisting of activated esters, epoxides, azlactones, activated hydroxyls, aldehydes, isocyanates, thioisocyanates, carboxylic acid chlorides, alkyl halides, maleimide, and α-iodoacetamide, and the backbone further comprises one or more pendent photoreactive groups selected from the group consisting of aryl ketones.

* * * * *

UNITED STATES PATENT AND TRADEMARK OFFICE
CERTIFICATE OF CORRECTION

PATENT NO.     : 6,465,178 B2
DATED          : October 15, 2002
INVENTOR(S)    : Chappa et al.

It is certified that error appears in the above-identified patent and that said Letters Patent is hereby corrected as shown below:

<u>Column 44,</u>
Line 31, "attache" should read -- attached --

Signed and Sealed this

Twenty-second Day of July, 2003

JAMES E. ROGAN
*Director of the United States Patent and Trademark Office*